(12) United States Patent
Zach et al.

(10) Patent No.: US 11,445,944 B2
(45) Date of Patent: *Sep. 20, 2022

(54) METHODS AND APPARATUS FOR ANALYTE CONCENTRATION MONITORING USING HARMONIC RELATIONSHIPS

(71) Applicant: ASCENSIA DIABETES CARE HOLDINGS AG, Basel (CH)

(72) Inventors: Juergen J. Zach, Lafayette, IN (US); Daniel V. Brown, Stamford, CT (US)

(73) Assignee: Ascensia Diabetes Care Holdings AG, Basel (CH)

( * ) Notice: Subject to any disclaimer, the term of this patent is extended or adjusted under 35 U.S.C. 154(b) by 195 days.

This patent is subject to a terminal disclaimer.

(21) Appl. No.: 16/796,906

(22) Filed: Feb. 20, 2020

(65) Prior Publication Data

US 2020/0268323 A1 Aug. 27, 2020

Related U.S. Application Data

(60) Provisional application No. 62/809,039, filed on Feb. 22, 2019.

(51) Int. Cl.
*A61B 5/145* (2006.01)
*A61B 5/1477* (2006.01)
(Continued)

(52) U.S. Cl.
CPC .......... *A61B 5/14532* (2013.01); *A61B 5/002* (2013.01); *A61B 5/1451* (2013.01);
(Continued)

(58) Field of Classification Search
CPC ... A61B 5/14532; A61B 5/002; A61B 5/1451; A61B 5/1473; A61B 5/1477;
(Continued)

(56) References Cited

U.S. PATENT DOCUMENTS 5,792,668 A * 8/1998 Fuller ................... A61B 5/053
436/95
8,233,958 B2 7/2012 Brauker et al.
(Continued)

FOREIGN PATENT DOCUMENTS

CA 3061574 A1 1/2019
EP 1218532 B1 7/2002
(Continued)

OTHER PUBLICATIONS

International Search Report and Written Opinion of related International Application No. PCT/EP2020/054459 dated May 20, 2020.
(Continued)

*Primary Examiner* — Franklin D Balseca
(74) *Attorney, Agent, or Firm* — Erise IP, P.A.

(57) ABSTRACT

Continuous glucose monitoring (CGM) may include applying a periodic excitation signal via an electrode of a CGM sensor to human interstitial fluid to drive an oxidation/reduction reaction, and measuring the current through the electrode. In some embodiments, the measured current is sampled and digitized, and various harmonics of the excitation signal's fundamental frequency are extracted. A set of relationships of at least two harmonics each is generated from the spectral amplitudes of a set of pairs, triplets, etc., of the harmonics, and the set of relationships is mapped to a glucose concentration such as based on the contents of a harmonic relationship database having a pre-existing set of harmonic relationships and glucose concentrations to which those sets of harmonic relationships correspond, for example. Numerous other embodiments are provided.

22 Claims, 15 Drawing Sheets

(51) Int. Cl.
   A61B 5/00      (2006.01)
   A61B 5/1473    (2006.01)
   G01N 31/00     (2006.01)
   G01N 33/66     (2006.01)
   G06F 1/16      (2006.01)
   G06F 17/14     (2006.01)
   H04Q 9/00      (2006.01)

(52) U.S. Cl.
   CPC .......... *A61B 5/1473* (2013.01); *A61B 5/1477* (2013.01); *A61B 5/6847* (2013.01); *A61B 5/7207* (2013.01); *A61B 5/7225* (2013.01); *A61B 5/7253* (2013.01); *A61B 5/7257* (2013.01); *A61B 5/742* (2013.01); *G01N 31/005* (2013.01); *G01N 33/66* (2013.01); *G06F 1/163* (2013.01); *G06F 17/142* (2013.01); *H04Q 9/00* (2013.01); *H04Q 2209/40* (2013.01)

(58) Field of Classification Search
   CPC ... A61B 5/6847; A61B 5/7207; A61B 5/7225; A61B 5/7253; A61B 5/7257; A61B 5/742; A61B 5/0002; A61B 5/0015; A61B 5/145; A61B 5/14546; G01N 31/005; G01N 33/66; G06F 1/163; G06F 17/142; H04Q 9/00; H04Q 2209/00; H04Q 2209/40; H04Q 2209/43; H04Q 2209/80; H04Q 2209/84
   See application file for complete search history.

(56) References Cited

U.S. PATENT DOCUMENTS

| | | |
|---|---|---|
| 8,583,205 B2 | 11/2013 | Budiman et al. |
| 2006/0094946 A1 | 5/2006 | Kellogg et al. |
| 2007/0167867 A1 | 7/2007 | Wolf |
| 2007/0270675 A1 | 11/2007 | Kane et al. |
| 2008/0077015 A1 | 3/2008 | Boric-Lubecke et al. |
| 2012/0283538 A1 | 7/2012 | Rose et al. |
| 2012/0197576 A1 | 8/2012 | Feldman |
| 2013/0071869 A1 | 3/2013 | Wu |
| 2013/0256156 A1 | 10/2013 | Wu et al. |
| 2014/0209460 A1 | 7/2014 | Wu et al. |
| 2014/0273042 A1 | 9/2014 | Saint |
| 2015/0073718 A1* | 3/2015 | Elder ................ A61B 5/1486 324/693 |
| 2015/0198555 A1 | 7/2015 | Lee et al. |
| 2015/0351673 A1 | 12/2015 | Vanslyke et al. |
| 2018/0275089 A1 | 9/2018 | Huang et al. |
| 2019/0008426 A1 | 1/2019 | Shiwaku |
| 2019/0125225 A1 | 5/2019 | Rebec et al. |
| 2020/0268290 A1 | 8/2020 | Zach et al. |

FOREIGN PATENT DOCUMENTS

| | | |
|---|---|---|
| EP | 1702561 A2 | 9/2006 |
| WO | WO2001088534 A | 11/2001 |
| WO | WO2008079435 A2 | 7/2008 |
| WO | WO2014128638 A1 | 8/2014 |
| WO | WO2017156584 A1 | 9/2017 |

OTHER PUBLICATIONS

Nakata et al., "Discrimination of Glucose from its Interferences Using an Amperometric Sensor Based on Electrochemical Nonlinearity", Analytical Chemistry, American Chemical Society, US, vol. 70, No. 20, Oct. 15, 1998, pp. 4304-4308, XP000789048, ISSN: 0003-2700, DOI: 10.1021/AC980442H.

Bond et al., "An integrated instrumental and theoretical approach to quantitative electrode kinetic studies based on large amplitude Fourier transformed a.c. volatammetry: A mini review", Electrochemistry Communications, Elsevier, Amsterdam, NL, vol. 57, May 8, 2015, pp. 78-83, XP029212452, ISSN: 1388-2481, DOI: 10.1016/J.Elecom.2015.04.017.

Nakata et al., "Experimental Demonstration and Simulation of Electrochemical Non-linear Reponses to Glucose and its Interferents with an Amperometric Senso", Analyst, London, GB, vol. 124, No. 8, Aug. 1, 1999, pp. 1175-1179, XP001039882, DOI: 10.1039/A903187A.

Stein et al.: "Microscale Enzymatic Optical Biosensors Using Mass-Transport Limiting Nanofilms. 1. Fabrication and Characterization Using Glucose as a Model Analyte"; Anal Chem. Feb. 15, 2007; 79(4): 1339-1348. DOI: 10.1021/ac061414z; https://www.ncbi.nlm.nih.gov/pmc/articles/PMC2518633/.

Haxha, et al.: "Optical Based Noninvasive Glucose Monitoring Sensor Prototype"; University of Bedfordshire, Luton , U.K.; IEEE Photonics Journal: vol. 8, No. 6, Dec. 2016. DOI: 10.1109/JPHOT.2016.26164911943-0655.

Parkes et al.: "A New Consensus Error Grid to Evaluate the Clinical Significance of Inaccuracies in the Measurement of Blood Glucose"; Diabetes Care, vol. 23, No. 8, Aug. 2000.

U.S. Appl. No. 17/014,947, filed Sep. 8, 2020, Wu.
U.S. Appl. No. 17/014,962, filed Sep. 8, 2020, Wu.

International Preliminary Report on Patentability of International Application No. PCT/EP2020/054459 dated Sep. 2, 2021.

Xu, Liang, et al.: "Optimization method for simultaneous kinetic analysis", Analytical Chem. 1996 ACS, Washington, DC, USA, vol. 68, No. 11, Jun. 1, 1996.

Nakata, S. et al.: Discrimination of Glucose from its Interferences Using an Amperometric Sensor Based on Electrochemical Nonlinearity, Analytical Chemistry, 1998 70 (20), 4304-4308 (Year: 1998).

* cited by examiner

400

| HARMONIC RATIO X RANGE | ANALYTE CONCENTRATION (UNITS) |
|---|---|
| $0 \leq X \leq 1$ | 1 |
| $1 < X \leq 2$ | 2 |
| $2 < X \leq 3$ | 3 |
| $3 < X \leq 4$ | 4 |
| $4 < X \leq 5$ | 5 |
| $5 < X$ | 6 |

FIG. 4

METHODS AND APPARATUS FOR ANALYTE CONCENTRATION MONITORING USING HARMONIC RELATIONSHIPS

The present application claims priority to U.S. Provisional Patent Application No. 62/809,039, filed Feb. 22, 2019, and titled "Methods and Apparatus for Analyte Concentration Monitoring Using Harmonic Relationships" which is hereby incorporated by reference herein in its entirety for all purposes.

FIELD

The present application relates generally to determining analyte concentration in an analyte-containing fluid.

BACKGROUND

Many applications call for the determination of the concentration of an analyte in an analyte-containing fluid. One application in particular is the determination of the concentration of glucose in a person's blood. Determining a person's blood glucose level is important for the management and control of diabetes. To that end, methods and apparatus for blood glucose monitoring (BGM) have been developed. However, BGM methods and apparatus require a blood sample typically obtained through "finger sticks," although blood may be taken from other areas of the body, such as, the palm or forearm; and the BGM results are not continuous, but rather single snapshots of blood glucose level at the time the blood sample is taken.

In order to more closely monitor a person's glucose level and detect shifts in glucose level, which may occur rapidly in people with diabetes, methods and apparatus for continuous glucose monitoring (CGM) have been developed. Although CGM systems are referred to as "continuous," measurements are typically performed every few minutes, rather than being truly continuous. CGM products, which have an implantable portion and a non-implantable portion, may be worn for several days, and up to multiple weeks, before being removed and replaced.

Existing CGM products provide frequent measurements of a person's glucose levels without the need for each such measurement to be accompanied by the drawing of blood, such as by finger sticks. These existing CGM products may still require occasional finger sticks and the use of a BGM system for the purpose of calibrating the CGM system. CGM products may include a sensor portion that is inserted so as to be located under the skin, and a non-implanted processing portion that is adhered to the outer surface of the skin, for example the abdomen, or the back of the upper arm. Unlike a BGM system that measures the glucose concentration in the blood, CGM systems measure the glucose concentration in interstitial fluid.

Improved CGM methods and apparatus are desired.

SUMMARY

In one example embodiment, a method of electronically probing an oxidation-reduction reaction in an analyte-containing fluid is provided. The method may include applying, by a first circuit, a periodic excitation signal to the analyte-containing fluid, wherein the periodic excitation signal has a fundamental frequency; generating, by a second circuit while the first circuit is applying the periodic excitation signal, a current measurement signal, wherein the current measurement signal has a magnitude indicative of a current produced by an oxidation-reduction reaction in the analyte-containing fluid, the magnitude dependent, at least in part, on an analyte concentration in the analyte-containing fluid; sampling, by a third circuit, the current measurement signal; providing, by the third circuit, digitized time-domain sample data representative of the current measurement signal; extracting a plurality of harmonic signals based, at least in part, on the digitized time-domain sample data, wherein the harmonic signals are harmonics of the fundamental frequency, and each harmonic signal has a corresponding strength; calculating a set of harmonic relationships based on at least a portion of the plurality of harmonic signals; accessing a harmonic relationship database, wherein the harmonic relationship database includes a plurality of sets of harmonic relationships, each set of harmonic relationships associated with a corresponding analyte concentration; and determining, based on the harmonic relationship database and the calculated set of harmonic relationships, a magnitude of an analyte concentration in the analyte-containing fluid.

In another example embodiment, a method of producing a set of predetermined harmonic relationship information that is correlated to corresponding values of an analyte concentration in an analyte-containing fluid, may include providing a plurality of analyte-containing fluid samples, wherein each one of the plurality of analyte-containing fluid samples has a known analyte concentration; and for each one of the plurality of analyte-containing fluid samples applying, by a first circuit, a periodic excitation signal to the analyte-containing fluid sample, wherein the periodic excitation signal has a fundamental frequency; generating, by a second circuit while the first circuit is applying the periodic excitation signal, a current measurement signal, wherein the current measurement signal has a magnitude indicative of a current produced by an oxidation-reduction reaction in the analyte-containing fluid while the first circuit is applying the periodic excitation signal, the magnitude dependent, at least in part, on the analyte concentration in the analyte-containing fluid; sampling, by a third circuit, the current measurement signal; providing, by the third circuit, digitized time-domain sample data representative of the current measurement signal; extracting a plurality of harmonic signals from the digitized time-domain sample data; calculating a set of harmonic relationships based on at least a portion of the plurality of harmonic signals; associating the set of harmonic relationships with the known analyte concentration of the analyte-containing fluid; and storing the set of harmonic relationships associated with the known analyte concentration in a harmonic relationship database.

In another example embodiment, a continuous analyte monitoring (CAM) system, may include a first circuit configured to apply a periodic excitation signal to an analyte-containing fluid; a second circuit configured to generate a current measurement signal, the current measurement signal having a magnitude indicative of a current in the analyte-containing fluid, the magnitude dependent, at least in part, on an analyte concentration in the analyte-containing fluid; a third circuit configured to sample the current measurement signal, and further configured to produce digitized time-domain sample data; and a processor coupled to a memory, the memory having a harmonic relationship database stored therein, and further having instructions stored therein that, when executed by the processor, cause the processor to: extract a plurality of harmonic signals from the digitized time-domain sample data; calculate a set of harmonic relationships based on at least a portion of the plurality of harmonic signals; access the harmonic relationship database, wherein the harmonic relationship database includes a plurality of sets of harmonic relationships, each set of harmonic relationships associated with a corresponding analyte concentration; and determine, based on the harmonic relationship database and the calculated set of harmonic relationships, a magnitude of the analyte concentration in the analyte-containing fluid.

In another example embodiment, a continuous glucose monitoring (CGM) system may include a CGM sensor configured for insertion into a region of interstitial fluid in a user; first electronic circuitry configured to couple to the CGM sensor and configured to be removably attached to an external surface of the user, wherein the first electronic circuitry includes a periodic excitation signal generator configured to couple to the CGM sensor, a current sensor configured to couple to the CGM sensor, and a sampling circuit configured to couple to the current sensor, the sampling circuit configured to output sampled time-domain data; and second electronic circuitry coupled to the first electronic circuitry, wherein the second electronic circuitry is configured to extract a predetermined number of harmonics from the sampled time-domain data, generate a set of harmonic relationships based on the extracted harmonics, and determine a glucose level based on the set of harmonic relationships.

In another example embodiment, a method of continuous glucose monitoring (CGM), may include generating, by a periodic excitation signal generator, a periodic excitation signal having an amplitude and a fundamental frequency; applying the periodic excitation signal to an electrode of a CGM sensor; sensing, by a current sensor circuit, a current through the CGM sensor to produce a measured current signal; sampling, by a sampling circuit, the measured current signal at a sampling rate, for a period of time, at a bit resolution, to produce a set of time-domain sample data; transforming the set of time-domain sample data to a set of frequency-domain data, wherein the set of frequency-domain data includes at least a strength of each one of a predetermined number of harmonics of the fundamental frequency; generating a set of harmonic relationships based on a strength of each of the predetermined number of harmonics; and determining a glucose level based on the set of harmonic relationships.

In some embodiments, an analyte monitoring system includes a first circuit configured to apply a periodic excitation signal to an analyte-containing fluid; a second circuit configured to generate a current measurement signal, the current measurement signal having a magnitude indicative of a current in the analyte-containing fluid, the magnitude dependent, at least in part, on an analyte concentration in the analyte-containing fluid; a third circuit configured to sample the current measurement signal, and further configured to produce digitized time-domain sample data; and a processor coupled to a memory, the memory having a harmonic relationship database stored therein, and further having instructions stored therein that, when executed by the processor, cause the processor to (a) extract a plurality of harmonic signals from the digitized time-domain sample data; (b) calculate a set of harmonic relationships based on at least a portion of the plurality of harmonic signals; and (c) determine, based on the calculated set of harmonic relationships, a magnitude of the analyte concentration in the analyte-containing fluid.

In some embodiments, an analyte monitoring system includes (1) a first circuit configured to apply a periodic excitation signal to an analyte-containing fluid, the periodic excitation signal having a fundamental frequency selected based at least in part on an approximate analyte concentration within the analyte-containing fluid; (2) a second circuit configured to generate a current measurement signal, the current measurement signal having a magnitude indicative of a current in the analyte-containing fluid, the magnitude dependent, at least in part, on the analyte concentration in the analyte-containing fluid; (3) a third circuit configured to sample the current measurement signal, and further configured to produce digitized time-domain sample data; and (4) a processor coupled to a memory, the memory having a harmonic relationship database stored therein, and further having instructions stored therein that, when executed by the processor, cause the processor to (a) extract a plurality of harmonic signals from the digitized time-domain sample data; (b) calculate a set of harmonic relationships based on at least a portion of the plurality of harmonic signals; (c) access the harmonic relationship database, wherein the harmonic relationship database includes a plurality of sets of harmonic relationships, each set of harmonic relationships associated with a corresponding analyte concentration; and (d) determine, based on the harmonic relationship database and the calculated set of harmonic relationships, a magnitude of the analyte concentration in the analyte-containing fluid.

In some embodiments, a method of electronically probing an oxidation-reduction reaction in an analyte-containing fluid includes (a) determining an approximate analyte concentration in an analyte-containing fluid; (b) determining a frequency of a periodic excitation signal to apply to the analyte-containing fluid based at least in part on the determined approximate analyte concentration; (c) applying, by a first circuit, the periodic excitation signal to the analyte-containing fluid; (d) generating, by a second circuit while the first circuit is applying the periodic excitation signal, a current measurement signal, wherein the current measurement signal has a magnitude indicative of a current produced by an oxidation-reduction reaction in the analyte-containing fluid, the magnitude dependent, at least in part, on analyte concentration in the analyte-containing fluid; (e) sampling, by a third circuit, the current measurement signal; (f) providing, by the third circuit, digitized time-domain sample data representative of the current measurement signal; (g) extracting a plurality of harmonic signals based, at least in part, on the digitized time-domain sample data, wherein the harmonic signals are harmonics of a fundamental frequency of the periodic excitation signal, and each harmonic signal has a corresponding strength; (h) calculating a set of harmonic relationships based on at least a portion of the plurality of harmonic signals; and (i) determining, based on the calculated set of harmonic relationships, a magnitude of an analyte concentration in the analyte-containing fluid.

In some embodiments, an analyte monitoring system includes (1) a first circuit configured to apply a periodic excitation signal to an analyte-containing fluid, the periodic excitation signal having a fundamental frequency selected based at least in part on an approximate analyte concentration within the analyte-containing fluid; (2) a second circuit configured to generate a current measurement signal, the current measurement signal having a magnitude indicative of a current in the analyte-containing fluid, the magnitude dependent, at least in part, on the analyte concentration in the analyte-containing fluid; (3) a third circuit configured to sample the current measurement signal, and further configured to produce digitized time-domain sample data; and (4) a processor coupled to a memory, the memory having instructions stored therein that, when executed by the processor, cause the processor to (a) extract a plurality of harmonic signals from the digitized time-domain sample data; (b) calculate a set of harmonic relationships based on at least a portion of the plurality of harmonic signals; and (c) determine, based on the calculated set of harmonic relationships, a magnitude of the analyte concentration in the analyte-containing fluid.

Other features, aspects, and advantages of embodiments in accordance with the present disclosure will become more fully apparent from the following detailed description, the subjoined claims, and the accompanying drawings by illustrating a number of example embodiments and implementations. Various embodiments in accordance with the present disclosure may also be capable of other and different applications, and its several details may be modified in various respects, all without departing from the spirit and scope of the claims. Accordingly, the drawings and descriptions are to be regarded as illustrative in nature, and not as restrictive. The drawings are not necessarily drawn to scale.

BRIEF DESCRIPTION OF THE DRAWINGS

FIG. 4 illustrates, at a high level, a data structure for mapping harmonic relationships to analyte concentrations in accordance with an example embodiment of the disclosure.

DETAILED DESCRIPTION

Overview

Figure 1A:
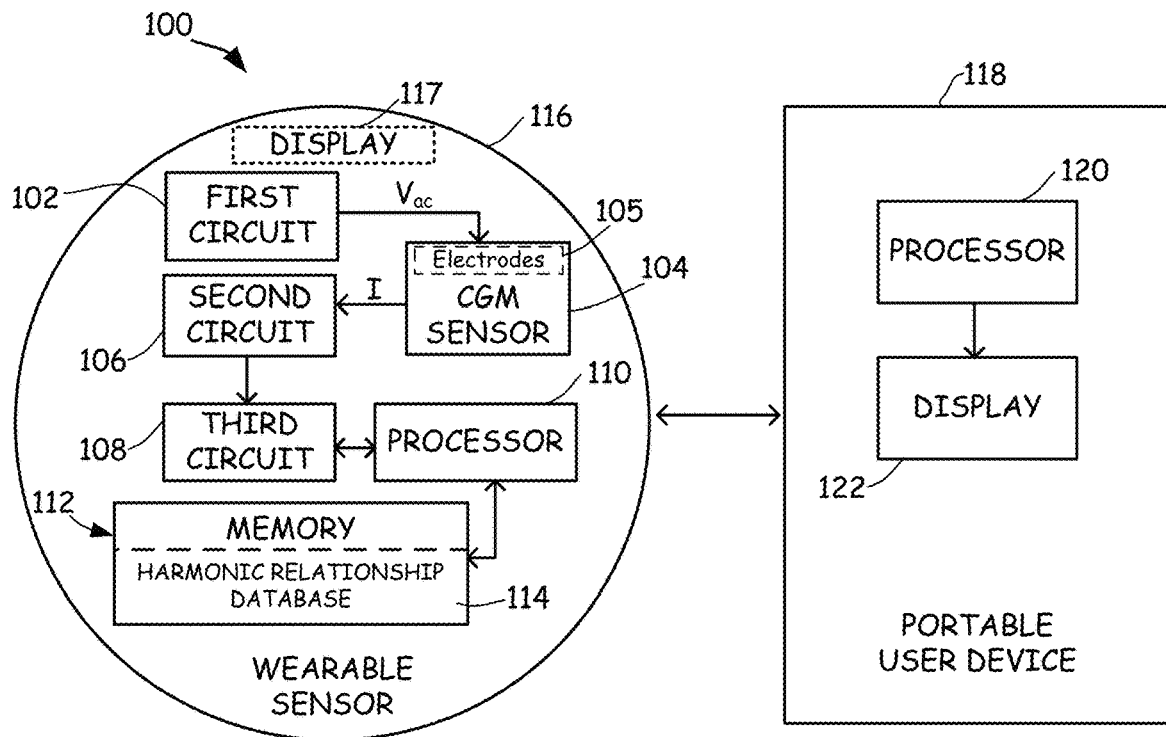
FIG. 1A illustrates a high-level block diagram of a first example embodiment of a CGM system with a harmonic relationship database stored in a wearable portion of the CGM system in accordance with the disclosure.

CGM systems provide a number of benefits for people, such as, but not limited to, reducing the number of finger sticks, and detecting rapid changes in glucose levels. However, one of the technical challenges of implementing a CGM system is that making glucose measurements on interstitial fluid rather than directly on a person's blood may result in a lower signal-to-noise ratio (SNR). A low signal-to-noise ratio may make processing of the signals obtained from a patient's interstitial fluid difficult.

In various embodiments provided herein and described in greater detail below, a low-frequency periodic excitation signal may be injected into a glucose-containing fluid (e.g., driving the glucose oxidation/reduction (redox) reaction in the fluid) and produce non-linear signal distortions in a corresponding measurement of a current in the fluid. Harmonics may be extracted from the complex waveform produced by the non-linear signal distortions, and may be used to generate a set of harmonic relationships, such as a set of harmonic ratios or other relationships between harmonics, correlated to the glucose concentration in the fluid. For different glucose concentrations, the set of harmonic relationships has a corresponding unique set of values. That is, the set of harmonic relationships may act as a vector in a glucose concentration space, where the vector coordinates (i.e., the evaluated set of harmonic relationships) point to, or define, a glucose concentration. More generally, sets of harmonic relationships may be generated for other analyte-containing fluids and employed to define analyte concentrations within such fluids.

In some embodiments, if multiple analytes are simultaneously present in a fluid to be analyzed, and the dependence of the harmonic relationship(s) is different for the different analytes and/or analyte concentrations, then the concentrations of multiple analytes may be determined simultaneously. Similarly one or more interferents may be detected, analyzed and/or corrected for during detection of analyte concentration. As an example, a fluid to be analyzed may contain glucose and at least one interferent, which can mimic glucose in an electrochemical measurement. However, glucose concentration may affect a set of harmonic relationships different than interferent concentration. As such, harmonic relationships may be used to determine glucose concentration as well as interferent concentration, and/or to determine glucose concentration while correcting for the presence of the interferent.

CGM Apparatus

In order to perform continuous glucose monitoring with a CGM system, a sensor is inserted into a patient. The inserted sensor provides electrodes disposed within a patient's interstitial fluid. Electrical circuitry may be coupled to the sensor. The electrical circuitry, or a housing or other packaging that contains the electrical circuitry, may be adhered to the patient's skin, and remain adhered for a period of days or longer. The sensor and the electrical circuitry, together, are configured as a wearable portion of the CGM system. Such a wearable portion may have additional electrical circuitry to implement additional features and functions.

The electrical circuitry may be used for processing electrical signals obtained by the sensor from the interstitial fluid. These signals are dependent upon a person's glucose level. These signals may be obtained automatically, for example, multiple times throughout the day. The electrical circuitry of the wearable portion may further be configured to store, display and/or communicate information regarding the patient's glucose levels.

As noted above, a BGM system determines the glucose level in a sample of a person's blood contemporaneously with a blood draw by, for example, a finger stick. Much effort has gone into accelerating the BGM measurement to obtain a single glucose measurement as quickly as possible for a person. The present state of the art for determining blood glucose level by a BGM system is less than five seconds. However, for CGM systems, there may be little benefit to measuring glucose in the interstitial fluid in significantly faster time scales than the intrinsic time lag between glucose in arterial blood versus glucose in interstitial fluid, which is about five minutes. Therefore, a meaningful time constraint for determining glucose level by CGM systems is on the order of one minute. That is, more time is available in CGM systems than BGM systems, and that extra time may be used for processing the low (as compared to BGM systems) SNR signals obtained from the interstitial fluid to determine the glucose level. Hence, embodiments provided herein may compensate for the relatively lower SNR in interstitial fluid compared to arterial blood (e.g., through use of a frequency-domain algorithm, which may provide a scalable SNR by the addition of more excitation cycles). Continuous monitoring systems for other type of analytes, interferents or other substances, such as maltose, galactose, hematocrit, medications such as acetaminophen, or the like, may be similarly employed in accordance with embodiments described herein.

FIG. 1A illustrates a high-level block diagram of an example CGM system 100 in accordance with embodiments provided herein. Although not shown in FIG. 1A, it is to be understood that the various electronic components and/or circuits are configured to couple to a power supply, such as but not limited to, a battery. CGM system 100 includes a first circuit 102 that may be configured to couple to a CGM sensor 104. First circuit 102 may be configured to apply a periodic excitation signal, such as a periodic voltage signal, to an analyte-containing fluid through CGM sensor 104. In this example embodiment, the analyte-containing fluid may be human interstitial fluid, and the periodic voltage signal may be applied to an electrode 105 of CGM sensor 104.

In some embodiments, the CGM sensor 104 may include two electrodes and the periodic voltage signal may be applied across the pair of electrodes. In such cases, current may be measured through the CGM sensor 104. In other embodiments, the CGM sensor 104 may include three electrodes such as a working electrode, a counter electrode and a reference electrode. In such cases, the periodic voltage signal may be applied between the counter electrode and the reference electrode, and current may be measured through the working electrode, for example. The CGM sensor 104 includes chemicals which react with a glucose-containing solution in a reduction-oxidation reaction, which affects the concentration of charge carriers and the time-dependent impedance of the CGM sensor 104. In some embodiments, such as when a three electrode sensor is employed, first circuit 102 may be configured to include a potentiostat, an output terminal of which forms an output terminal of first circuit 102.

The periodic voltage signal generated by first circuit 102 is a time-varying signal that may be, for example, but not limited to, sinusoidal, square, sawtooth, triangular or the like with or without a DC offset. To simplify subsequent signal processing, the periodic signal may be stabilized before being applied to the analyte containing fluid (e.g., to avoid introducing harmonics not produced by the redox reaction). However, in embodiments where the periodic voltage signal has a fundamental frequency on the order of the chemical reaction dynamics of the sensor, for example much less than 1 kHz but greater than 0.01 Hz, a stabilization process or waiting period may be reduced or eliminated because generation of such low frequency periodic signals may be made very "clean" from the start. At frequencies much higher than 1 kHz, the chemical reaction dynamics of the sensor often do not influence the current response, so that a signal stabilization period is not required. In some embodiments, the periodic voltage signal generated by first circuit 102 may include a DC offset voltage.

In some embodiments, the periodic voltage signal may have a fixed or slowly varying frequency. In other embodiments, the periodic voltage signal may have a frequency that changes between different discrete frequencies (e.g., being maintained at each frequency for multiple periods of the periodic voltage signal, such as 10 or more, for example). Example excitation frequencies for the periodic voltage signal range from about 0.1 Hz to 10 Hz, and in some embodiments about 0.5 to 2 Hz, although other values may be used. Example peak voltages range from about 0.5 to 500 milliVolts, and in some embodiments up to about 1 Volt, although larger or smaller values may be used (e.g., with or without a DC offset).

A current through CGM sensor 104 in the analyte-containing fluid responsive to the periodic voltage signal is non-linear and may be conveyed from CGM sensor 104 to a second circuit 106. Second circuit 106 may be configured to generate a current measurement signal that has a magnitude indicative of the magnitude of the current conveyed from CGM sensor 104. In some embodiments, second circuit 106 may include a resistor having a known nominal value and a known nominal precision (e.g., 0.1% to 5%, or even smaller than 0.1%, in some embodiments), through which the current conveyed from CGM sensor 104 is passed. A voltage developed across the resistor of second circuit 106 represents the magnitude of the current, and may be referred to as the current measurement signal.

The non-linear components of the current measurement signal depend on analyte (e.g., glucose and/or other analyte) concentration within the analyte-containing fluid being analyzed. As will be described further below, in accordance with embodiments provided herein, the non-linear characteristics of the current measurement signal (which depend on analyte concentration) may be quantified by extracting higher order harmonics of the fundamental frequency of the applied periodic signal. For example, a "strength" of each harmonic of the fundamental frequency, such as amplitude, power, etc., may be extracted for integer multiples of the fundamental frequency f (such as harmonic n*f where n=2, 3, 4, 5, 6, 7, 8, 9, 10, or more). The entire spectrum or a portion of frequencies of the non-linear current measurement signal may be employed, as may specific frequencies (e.g., using Fourier, fast Fourier, discrete Fourier, Goertzel or other transforms).

A third circuit 108 may be coupled to second circuit 106, and may be configured to sample the current measurement signal, and may produce digitized time-domain sample data that is representative of the current measurement signal. For example, third circuit 108 may be any suitable, well-known A/D converter circuit configured to receive the current measurement signal, which is an analog signal, and convert it to a digital signal having a desired number of bits as an output. The number of bits output by third circuit 108 may be sixteen in some embodiments, but more or fewer bits may be used in other embodiments. In some embodiments, third circuit 108 may sample the current measurement signal at a sampling rate in the range of about 10 samples per second to 1000 samples per second. Faster or slower sampling rates may be used. For example, sampling rates such as about 10 kHz to 100 kHz may be used and down-sampled to further reduce signal-to-noise ratio.

Third circuit 108 may sample the current measurement signal at the sampling rate for a period of time referred to as the sampling window. In various embodiments, the sampling window may be between about 10 seconds and 300 seconds. Longer or shorter sampling windows may be used.

Still referring to FIG. 1A, a processor 110 may be coupled to third circuit 108, and may be further coupled to a memory 112. In some embodiments, processor 110 and third circuit 108 are configured to directly communicate with each other via a wired pathway. In some embodiments the wired pathway between processor 110 and third circuit 108 is a serial path in which one bit of digital data is transferred at a time. In other embodiments, the wired pathway between processor 110 and third circuit 108 is a parallel path in which two or more bits of digital data are transferred at a time. In still other embodiments, the coupling of processor 110 and third circuit 108 may be by way of memory 112. In this arrangement, third circuit 108 writes digital data to memory 112, and processor 110 reads the digital data from memory 112.

Memory 112 may have stored therein a harmonic relationship database 114 (described in detail below). Memory 112 also may have stored therein a plurality of instructions. In various embodiments, processor 110 may be a computational resource such as but not limited to a microprocessor, a microcontroller, an embedded microcontroller, a digital signal processor (DSP), a field programmable gate array (FPGA) configured to perform as a microcontroller, or the like.

In some embodiments, the plurality of instructions stored in memory 112 may include instructions that, when executed by the processor 110, cause the processor 110 to (a) extract a plurality of harmonic signals from the digitized time-domain sample data generated by third circuit 108; (b) calculate or otherwise determine a set of harmonic relationships based on at least a portion of the plurality of harmonic signals; (c) access the harmonic relationship database 114; and (d) determine, based on the harmonic relationship database 114 and the determined set of harmonic relationships, a magnitude of the analyte concentration in the analyte-containing fluid sensed by CGM sensor 104.

Memory 112 may be any suitable type of memory, such as but not limited to, one or more of a volatile memory and/or a non-volatile memory. For example, memory 112 may include a combination of different types of memory such as volatile memory and non-volatile memory. Volatile memory may include, but is not limited to a static random access memory (SRAM), or a dynamic random access memory (DRAM). Non-volatile memory may include, but is not limited to, an electrically programmable read-only memory (EPROM), an electrically erasable programmable read-only memory (EEPROM), a flash memory (e.g., a type of EEPROM in either of the NOR or NAND configurations, and/or in either the stacked or planar arrangements, and/or in either the single-level cell (SLC), multi-level cell (MLC), or combination SLC/MLC arrangements), a resistive memory, a filamentary memory, a metal oxide memory, a phase change memory (such as a chalcogenide memory), or a magnetic memory. Memory 112 may be packaged as a single chip or as multiple chips, for example. In some embodiments, memory 112 may be embedded, with one or more other circuits, in an integrated circuit, such as, for example, an application specific integrated circuit (ASIC).

As noted above, memory 112 may have a plurality of instructions stored therein that, when executed by processor 110, cause processor 110 to perform various actions specified by one or more of the stored plurality of instructions. Memory 112 may further have portions reserved for one or more "scratchpad" storage regions that may be used for read or write operations by processor 110 responsive to execution of one or more instructions of the plurality of instructions.

In the embodiment of FIG. 1A, first circuit 102, CGM sensor 104, second circuit 106, third circuit 108, processor 110, and memory 112 including harmonic relationship database 114, may be disposed within a wearable sensor portion 116 of CGM system 100. In some embodiments, wearable sensor portion 116 may include a display 117 for displaying information such as glucose concentration information (e.g., without use of external equipment). Display 117 may be any suitable type of human-perceivable display, such as but not limited to, a liquid crystal display (LCD), a light-emitting diode (LED) display, or an organic light emitting diode (OLED) display.

Still referring to FIG. 1A, CGM system 100 further includes a portable user device portion 118. A processor 120 and a display 122 may be disposed within portable user device portion 118. Display 122 may be coupled to processor 120. Processor 120 may control the text or images shown by display 122. Wearable sensor portion 116, and portable user device portion 118, may be communicatively coupled. In some embodiments the communicative coupling of wearable sensor portion 116, and portable user device portion 118, may be by way of wireless communication. Such wireless communication may be by any suitable means including but not limited to standards-based communications protocols such as the Bluetooth® communications protocol. In various embodiments, wireless communication between wearable sensor portion 116, and portable user device portion 118, may alternatively be by way of near-field communication (NFC), radio frequency (RF) communication, infra-red (IR) communication, or optical communication. In some embodiments, wearable sensor portion 116 and portable user device portion 118 may be connected by one or more wires.

Display 122 may be any suitable type of human-perceivable display, such as but not limited to, a liquid crystal display (LCD), a light-emitting diode (LED) display, or an organic light emitting diode (OLED) display.

Figure 1B:
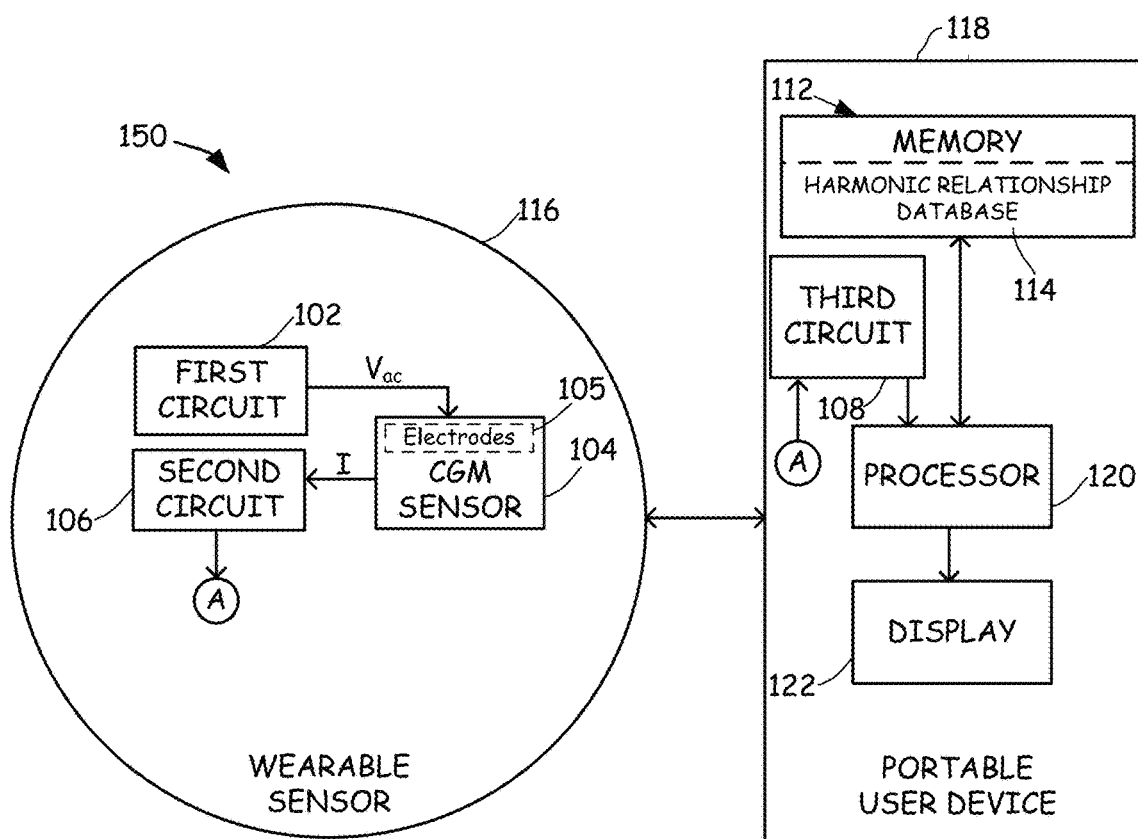
FIG. 1B illustrates a high-level block diagram of a second example embodiment of a CGM system with a harmonic relationship database stored in a portable user device portion of the CGM system in accordance with the disclosure.

Referring now to FIG. 1B, an example CGM system 150 is shown that is similar to the embodiment illustrated in FIG. 1A, but having a different partitioning of components. In CGM system 150, the wearable sensor portion 116 includes the first circuit 102 coupled to the CGM sensor 104, and the second circuit 106 coupled to the CGM sensor 104. The portable user device portion 118 of CGM system 150 includes the third circuit 108 coupled to processor 120, and the display 122 coupled to processor 120. Processor 120 is further coupled to memory 112 that has the harmonic relationship database 114 stored therein. In some embodiments, processor 120 in CGM system 150 may also perform the previously-described functions performed by processor 110 of CGM system 100 of FIG. 1A, for example. Wearable sensor portion 116 of CGM system 150 may be smaller and lighter, and therefore less invasive, than wearable sensor portion 116 of CGM system 100 of FIG. 1A because third circuit 108, processor 110, memory 112, etc., are not included therein.

Figure 1C:
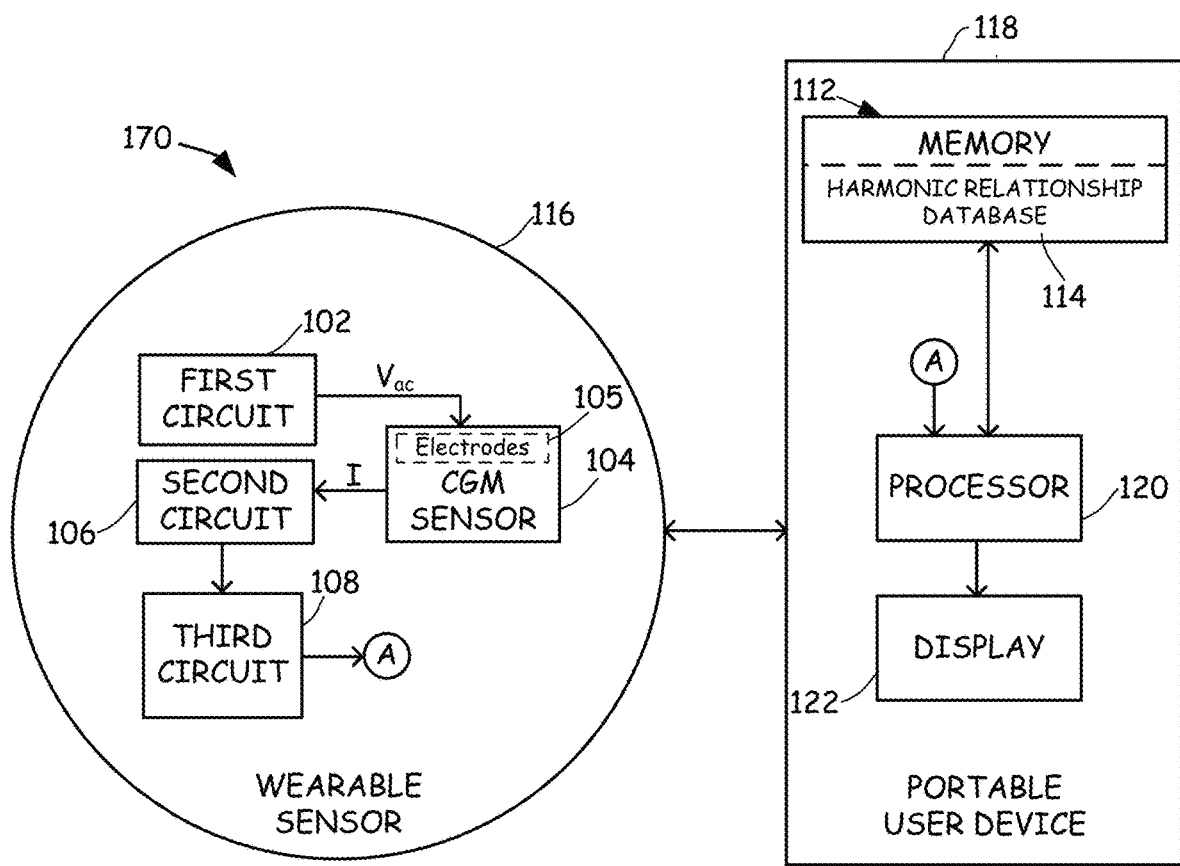
FIG. 1C illustrates a high-level block diagram of a third example embodiment of a CGM system in accordance with the disclosure.

Referring now to FIG. 1C, an example CGM system 170 is shown that is similar to the embodiment illustrated in FIG. 1B, but having a different partitioning of components. In CGM system 170, the wearable sensor portion 116 includes the first circuit 102 coupled to the CGM sensor 104, the second circuit 106 coupled to the CGM sensor 104, and the third circuit 108 coupled to the second circuit 106. The portable user device portion 118 of CGM system 170 includes the processor 120, and the display 122 coupled to processor 120. Processor 120 is further coupled to memory 112 that has the harmonic relationship database 114 stored therein. Wearable sensor portion 116 of CGM system 170 may be smaller and lighter, and therefore less invasive, than wearable sensor portion 116 of CGM system 100 of FIG. 1A because processor 110, memory 112, etc., are not included therein.

Figure 2:
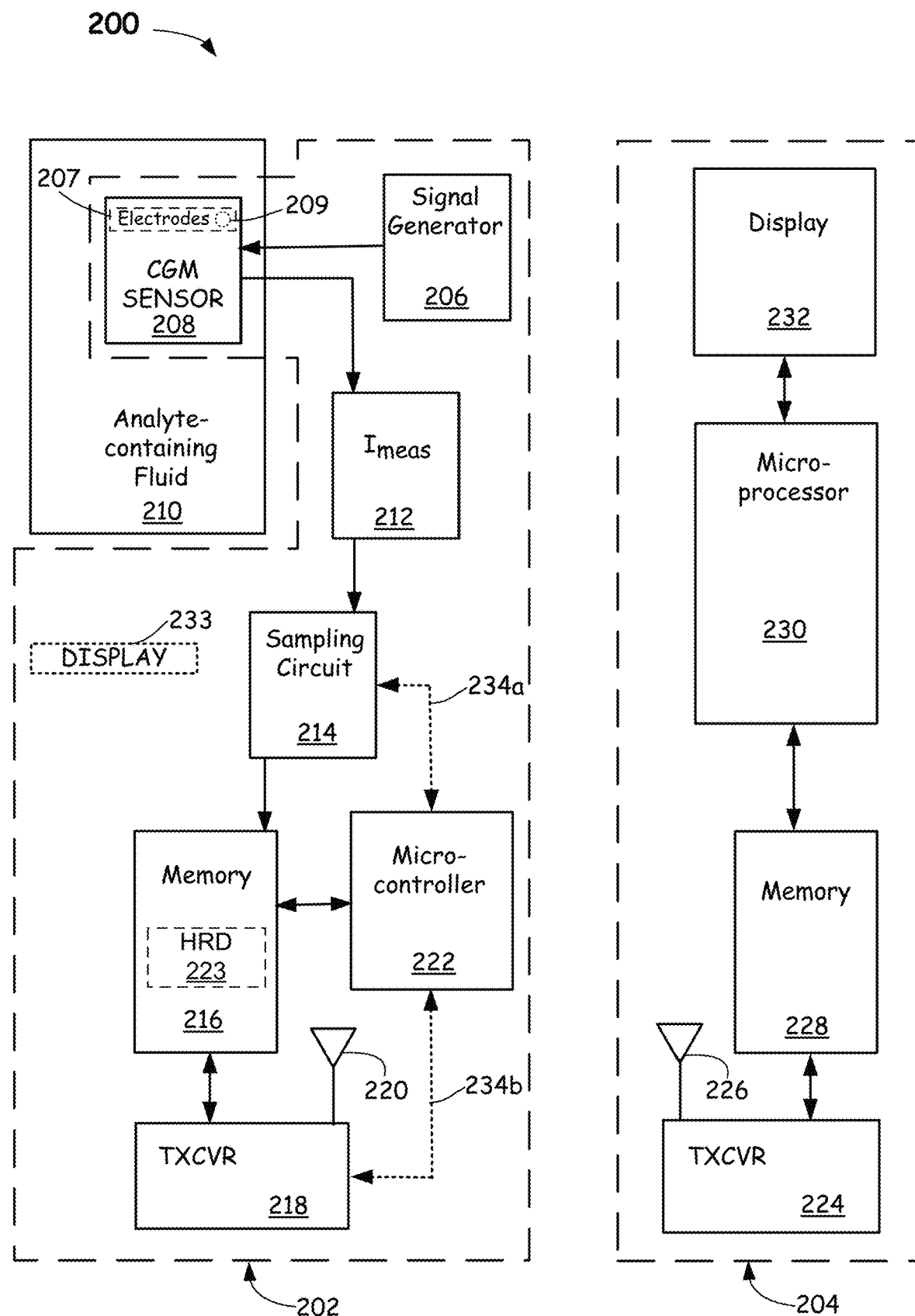
FIG. 2 illustrates a high-level block diagram of another CGM system in accordance with an example embodiment of the disclosure.

Referring to FIG. 2, an example CGM system 200 provided herein includes a wearable portion 202 (shown within a dashed line box) and a portable user device portion 204 (shown within a dashed line box). Wearable portion 202 includes a periodic signal generator 206 that is coupled to electrodes 207 of a CGM sensor 208, one of which may be working electrode 209, for example. The electrodes 207 of CGM sensor 208 are shown to be in an analyte-containing fluid 210. In some embodiments, the analyte-containing fluid is human interstitial fluid, and the analyte is glucose. The electrodes 207 of CGM sensor 208 are further coupled to current measuring circuit 212. (Signal generator 206 and current measuring circuit 212 may be similar to first circuit 102 and second circuit 106, respectively, of FIGS. 1A, 1B and 1C.)

Current measuring circuit 212 receives a current from electrodes 207 that is generated by an oxidation-reduction reaction in the analyte-containing fluid 210, and that current is responsive to the voltage applied to the electrodes 207 by signal generator 206. Current measuring circuit 212 generates a current measurement signal, the magnitude of which is responsive to the voltage applied to the electrodes 207 by signal generator 206. Current measuring circuit 212 is coupled to a sampling circuit 214.

Sampling circuit 214, similar to third circuit 108 of FIGS. 1A, 1B and 1C, is configured to receive as an input, the current measurement signal generated by current measuring circuit 212. Sampling circuit 214 may be configured to sample the current measurement signal, and may produce digitized time-domain sample data that is representative of the current measurement signal. In some embodiments, sampling circuit 214 may be an A/D converter with any suitable bit resolution. In some embodiments, sampling circuit 214 may have a bit resolution of sixteen bits. More or fewer bits may be used. Sampling circuit 214 may sample the current measurement signal at a sampling rate in the range of about 10 samples per second to 1000 samples per second, for example. Faster or slower sampling rates may be used. For example, sampling rates such as about 10 kHz to 100 kHz may be used and down-sampled to further reduce signal-to-noise ratio. Further, sampling circuit 214 may sample the current measurement signal at the sampling rate for a period of time referred to as the sampling window. In various embodiments, the sampling window may be between about 10 seconds and 300 seconds. Other sampling rates and/or sampling windows may be used.

Still referring to FIG. 2, sampling circuit 214 is coupled to a memory 216. In some embodiments, sampling circuit 214 may be configured to write the digitized time-domain sample data that is representative of the current measurement signal into memory 216.

Memory 216 may be any suitable type of memory, such as but not limited to, a volatile memory or a non-volatile memory, as described previously with reference to FIGS. 1A, 1B and 1C. For example, memory 216 may include a combination of different types of memory such as volatile memory and non-volatile memory.

Memory 216 may have a plurality of instructions stored therein. Memory 216 of wearable portion 202 is further coupled to transceiver 218, which is coupled to antenna 220. Memory 216 is still further coupled to a microcontroller 222. The plurality of instructions stored in memory 216, when executed by microcontroller 222, cause microcontroller 222 to perform various actions specified by one or more of the stored plurality of instructions. In some embodiments, memory 216 may have a harmonic relationship database (HRD) 223 stored therein.

Still referring to FIG. 2, microcontroller 222 may be a standalone microcontroller, an embedded microcontroller, a digital signal processor (DSP), a field programmable gate array (FPGA) configured to perform as a microcontroller, or the like.

In example CGM system 200, transceiver 218 may be a radio transmitter/receiver that is configured to read information from memory 216 and transmit that data to portable user device portion 204 by way of transceiver 224 and its antenna 226. In some embodiments, transceiver 224 may write the information it receives from transceiver 218 into a memory 228, which is disposed in portable user device portion 204. In an alternative embodiment, described below, one or more other electrical components may facilitate the transfer of data between sampling circuit 214 and memory 216. In various embodiments, wireless communication between transceivers 218, 224 may be by way of Bluetooth® communication, near-field communication (NFC), radio frequency (RF) communication, infra-red (IR) communication, optical communication or the like. In some embodiments, wearable sensor portion 202 and portable user device portion 204 may be connected by one or more wires.

Memory 228 may be further coupled to a microprocessor 230. Memory 228 may be any suitable type of memory, such as but not limited to, a volatile memory and/or a non-volatile memory, as described previously with reference to FIGS. 1A, 1B and 1C.

Microprocessor 230 may be a computational resource implemented in any suitable manner. For example, microprocessor 230 may be, but is not limited to, a standalone chip, a plurality of logically-coupled chips, an FPGA configured to perform the function of a microprocessor, an embedded processor, a digital signal processor, or the like.

Microprocessor 230 may be further coupled to a display 232. Display 232 may be any suitable display. For example, display 232 may be a human-perceivable display, such as but not limited to, an LCD, or an LED or OLED display.

In some embodiments, wearable sensor portion 202 may include a display 233, similar to display 117 of FIG. 1A, for example, for displaying information such as glucose concentration information (e.g., without use of external equipment). The display 233 may be any suitable type of human-perceivable display, such as but not limited to, an LCD, or an LED or OLED display.

In some alternative embodiments, data from sampling circuit 214 may not be written directly to memory 216, but may be read from sampling circuit 214 by microcontroller 222, and then written to memory 216 (or to portable user device portion 204) by microcontroller 222. This data pathway is illustrated by the dashed arrows 234a, 234b in FIG. 2.

Figure 3:
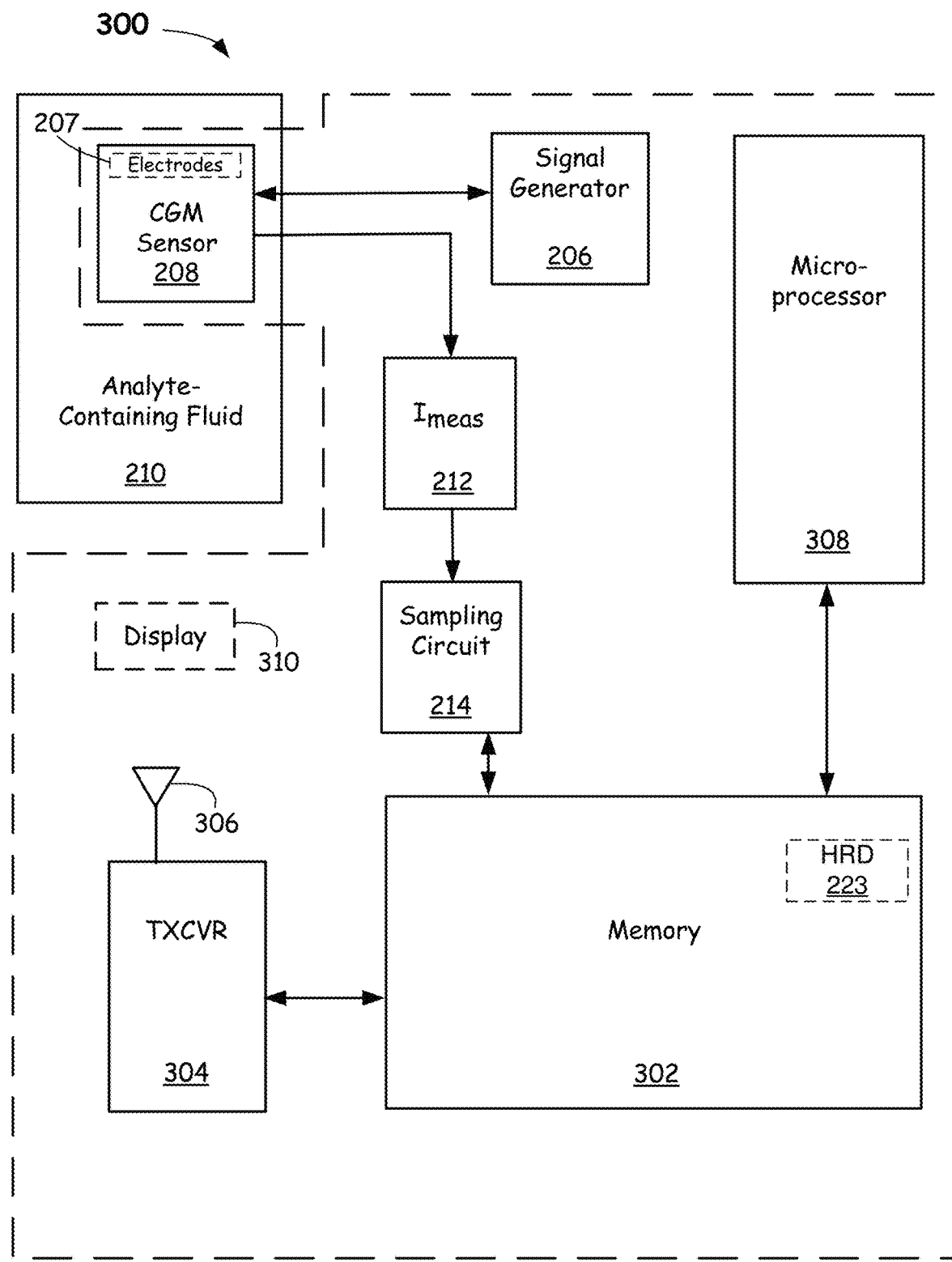
FIG. 3 illustrates a high-level block diagram of yet another CGM system in accordance with an example embodiment of the disclosure.

The example CGM systems 100, 150, 170 and 200 of FIGS. 1A, 1B, 1C and 2 respectively, each illustrate a two-piece CGM system having a wearable portion and a portable user device portion. FIG. 3 illustrates an example one-piece CGM system 300 that includes the functionality of the previously described wearable portions and portable user portions. That is, example one-piece CGM system 300 is configured to apply a periodic excitation voltage to an analyte-containing fluid, generate a current measurement signal representative of the resulting current, extract harmonics based on the current measurement signal, generate a set of harmonic relationships from the extracted harmonics, and/or, based at least in part on the generated set of harmonic relationships, determine the magnitude of an analyte concentration in the analyte-containing fluid. In some embodiments, the one-piece CGM system 300 may be further configured to wirelessly transmit the determined analyte concentration to one or more receivers that are physically separate from CGM system 300.

As illustrated in FIG. 3, example CGM system 300 (shown within the dashed line box) includes a periodic signal generator 206 coupled to the electrodes 207 of CGM sensor 208. FIG. 3 shows the electrodes 207 of CGM sensor 208 disposed in analyte-containing fluid 210. A current measuring circuit 212 is coupled to electrodes 207 of CGM sensor 208 and further coupled to sampling circuit 214, which is coupled to memory 302. A transceiver 304 and its corresponding antenna 306 may also be included in CGM system 300. Transceiver 304 is coupled to memory 302. Memory 302 is further coupled to a microprocessor 308. Memory 302 may be similar to memory 216 and/or 228 of FIG. 2 and include a harmonic relationship database (HRD) 223, for example. Signal generator 206, current measuring circuit 212, sampling circuit 214, memory 302, harmonic relationship data (HRD) 223 and microprocessor 308 may be employed to determine an analyte concentration in the analyte-containing fluid 210 as described above. Transceiver 304 and antenna 306 may then wirelessly transmit the determined analyte concentration to one or more receivers that are physically separate from CGM system 300. In some embodiments, CGM system 300 may include a display 310 for displaying analyte and/or other information (e.g., analyte concentration). For example, display 310 may be an LCD, or an LED or OLED display, or another suitable display.

Figure 5:
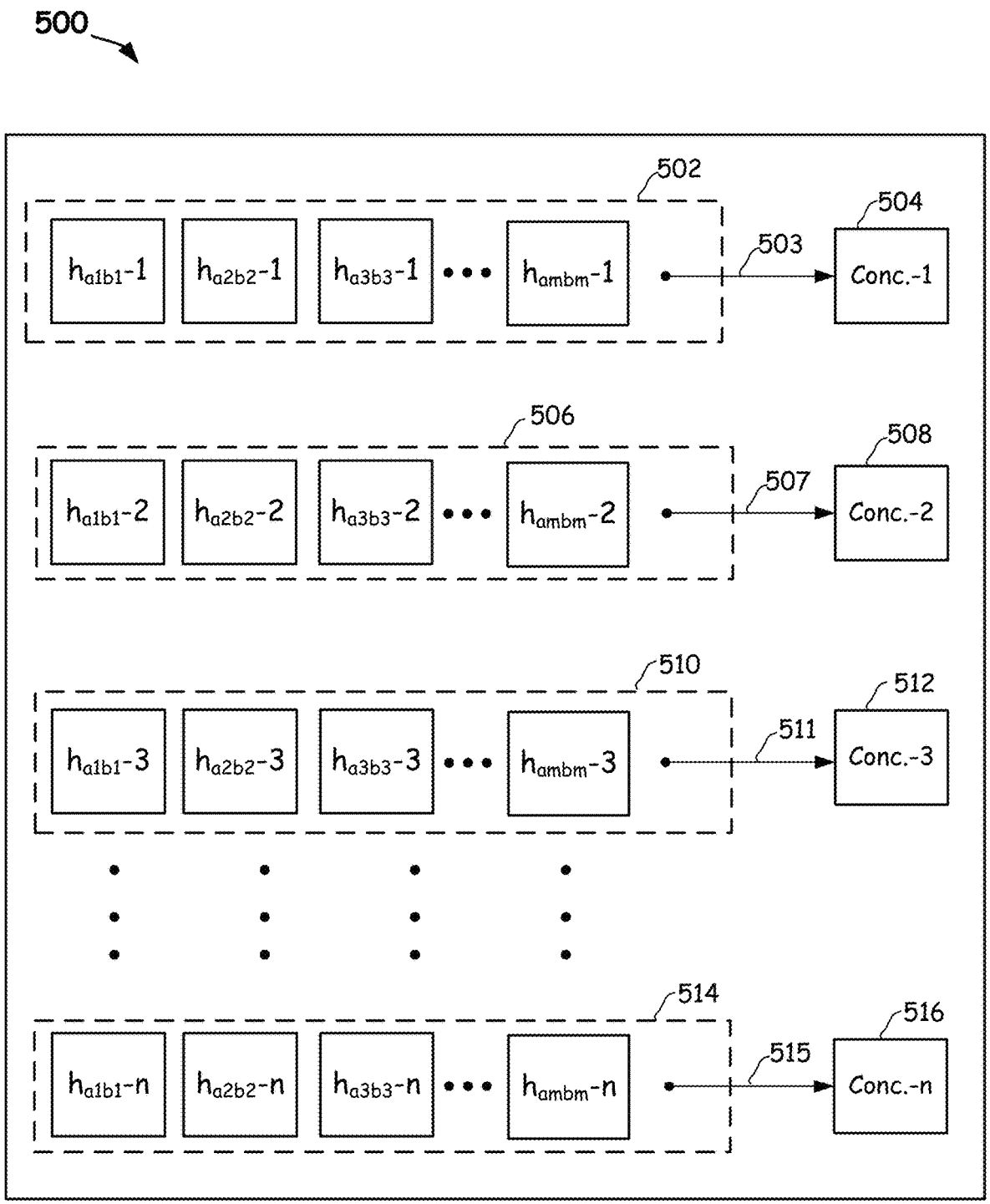
FIG. 5 illustrates, at a high level, a harmonic relationship database for mapping harmonic relationships to analyte concentrations in accordance with an example embodiment of the disclosure.
Figure 6A:
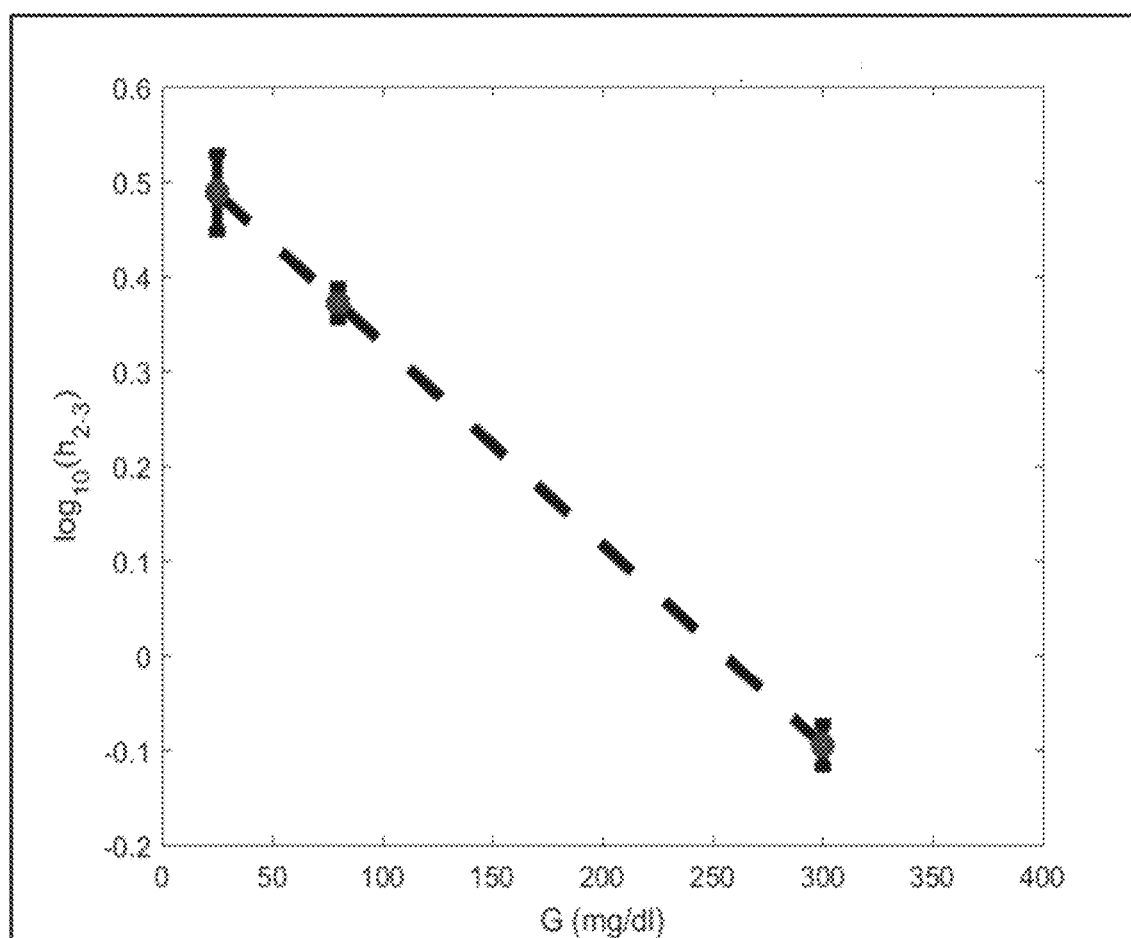
FIG. 6A illustrates a semi-log plot of a ratio of the strength of the second harmonic to the strength of the third harmonic of a fundamental frequency of a periodic excitation signal applied to a glucose containing fluid at three different concentrations in accordance with an example embodiment of the disclosure.
Figure 6B:
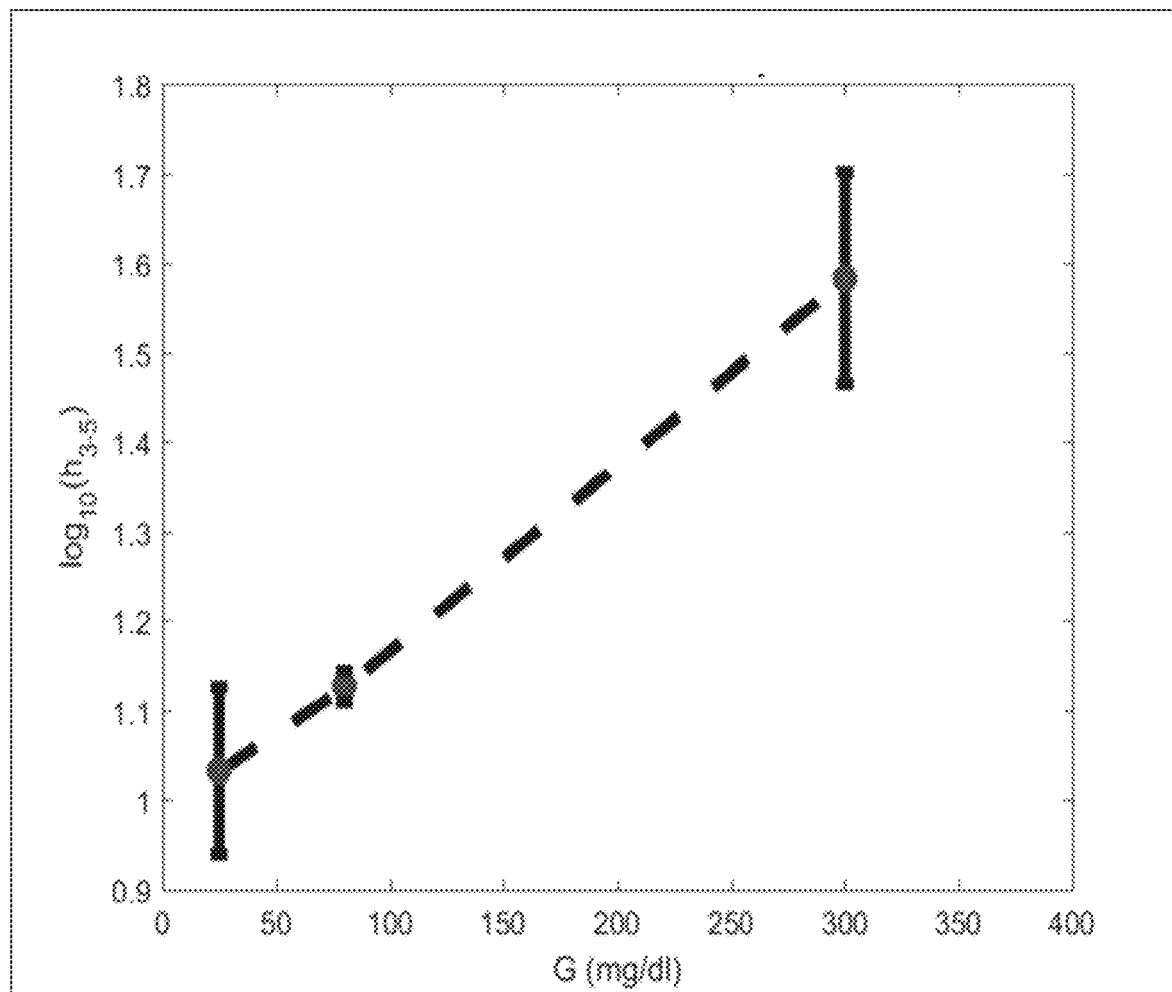
FIG. 6B illustrates a semi-log plot of a ratio of the strength of the third harmonic to the strength of the fifth harmonic of a fundamental frequency of a periodic excitation signal applied to a glucose containing fluid at three different concentrations in accordance with an example embodiment of the disclosure.
Figure 6C:
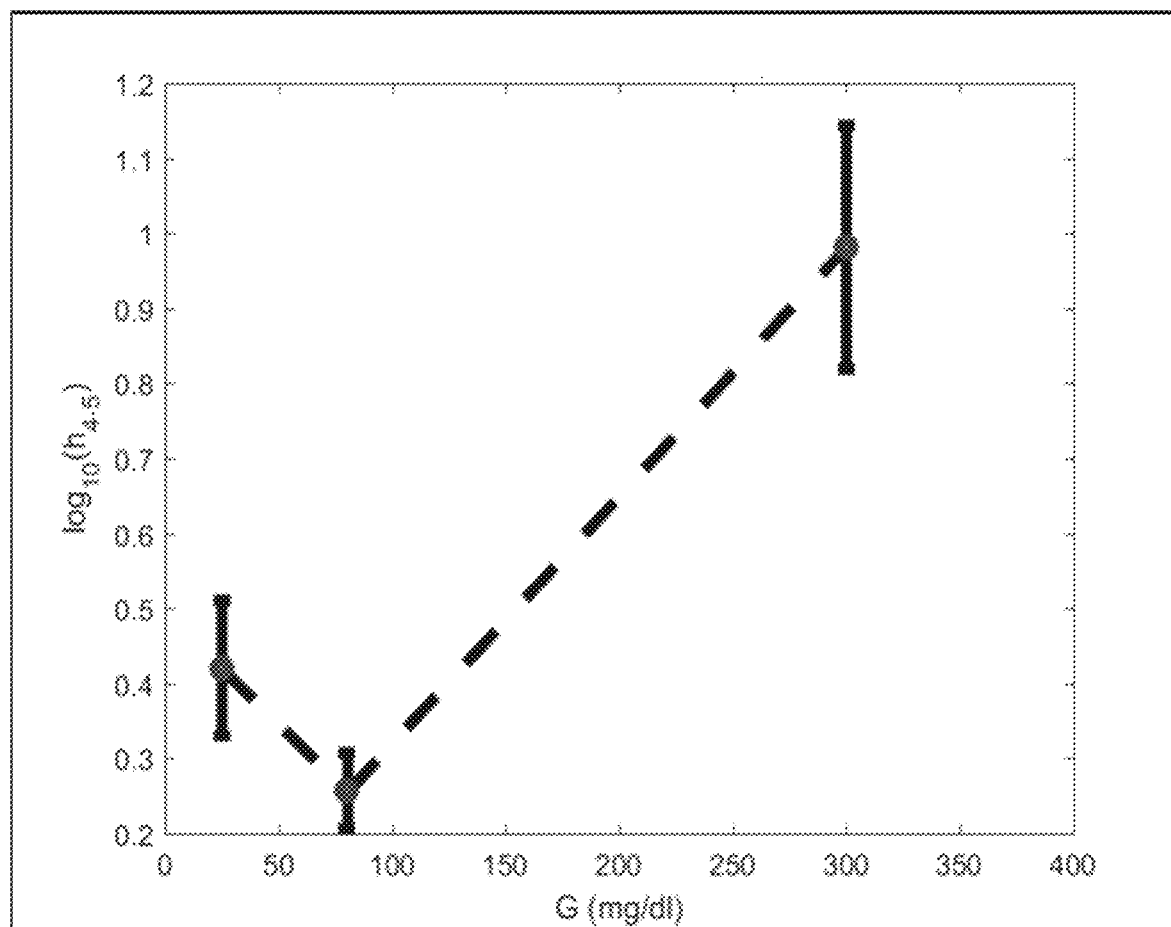
FIG. 6C illustrates a semi-log plot of a ratio of the strength of the fourth harmonic to the strength of the third harmonic of a fundamental frequency of a periodic excitation signal applied to a glucose containing fluid at three different concentrations in accordance with an example embodiment of the disclosure.
Figure 6D:
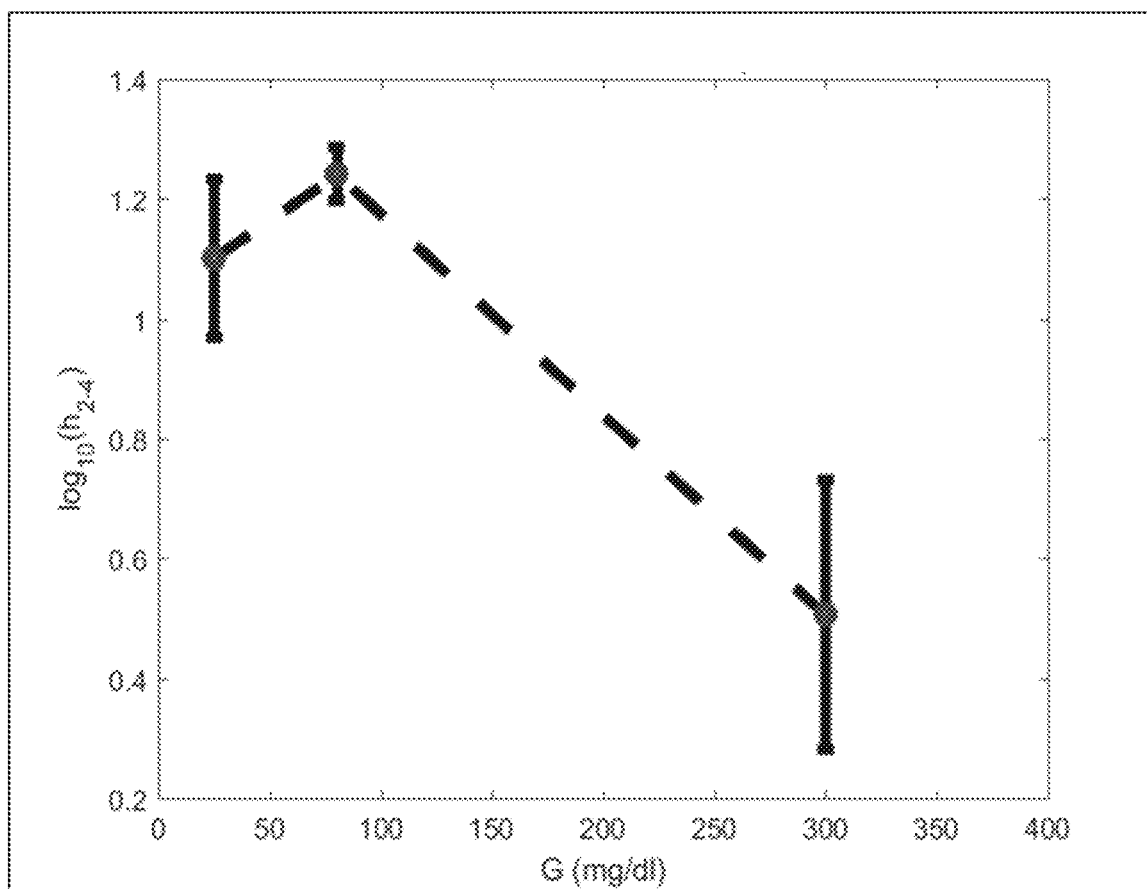
FIG. 6D illustrates a semi-log plot of a ratio of the strength of the second harmonic to the strength of the fourth harmonic of a fundamental frequency of a periodic excitation signal applied to a glucose containing fluid at three different concentrations in accordance with an example embodiment of the disclosure.

FIGS. 4 and 5 illustrate data structures for mapping a set of harmonic relationships to corresponding analyte concentration values in accordance with embodiments provided herein. FIG. 4 shows the relationship between harmonic ratios and the analyte concentrations at a high-level of abstraction. FIG. 5 shows the relationship between harmonic ratios and the analyte concentrations with additional detail. While FIGS. 4 and 5 are described with regard to ratios of harmonics, it will be understood that other harmonic relationships may be used including, for example, multiplication, addition or subtraction of the characteristics (e.g., strengths) of two or more harmonics, trigonometric, logarithmic, exponential, or polynomial functions based on the characteristics (e.g., strengths) of two or more harmonics, combinations of the above, or the like.

FIG. 4 illustrates a simplified high-level block diagram of an example data structure 400 useful for determining an analyte concentration of an analyte-containing fluid based at least in part on one or more harmonic ratios. In some embodiments, harmonic relationship database 114 and/or 223 may include one or more data structures similar to database structure 400. As described below with reference to FIG. 5, in general, several harmonic ratios may be used to determine analyte concentration.

Data structure 400 may be, for example, a table (e.g., a lookup table) having a predetermined number of rows and columns. In the example data structure 400 shown in FIG. 4 there are six rows 402, 404, 406, 408, 410, and 412, and two columns 414, and 416. In the example data structure 400, each row contains a first entry that contains a range specification for each one of a set of at least one harmonic ratios. For example, X represents a set of harmonic ratios that can be associated with a particular analyte concentration, or with a range of analyte concentrations. In the illustrated example of FIG. 4, X in row 402 is characterized as being between 0 inclusive and 1 inclusive, which is associated with an analyte concentration of 1. Likewise, X in row 404 is characterized as being between 1 and 2 inclusive, which is associated with an analyte concentration of 2. X in row 406 is characterized as being between 2 and 3 inclusive, which is associated with an analyte concentration of 3. X in row 408 is characterized as being between 3 and 4 inclusive, which is associated with an analyte concentration of 4. X in row 410 is characterized as being between 4 and 5 inclusive, which is associated with an analyte concentration of 5. Similarly, X in row 412 is characterized as being greater than 5, which is associated with an analyte concentration of 6. The example values provided in example data structure 400 are simply for illustrating the use of a set of harmonic ratios to map to corresponding analyte concentrations. Various embodiments may have more or fewer entries in such a data structure.

FIG. 5 illustrates a high-level block diagram of an example harmonic relationship database 500 useful for determining an analyte concentration of an analyte-containing fluid based at least in part on one or more harmonic ratios. Example analytes include glucose, maltose, galactose, hematocrit, medications such as acetaminophen, or the like. In some embodiments, the harmonic relationship database 114 and/or 223 of FIGS. 1A-3 may be similarly configured.

As noted above, providing a periodic excitation, such as an AC excitation signal, to an analyte-containing fluid may produce a time-domain current signal that is characteristic of the concentration of an analyte in the analyte-containing fluid. Harmonics of the excitation signal's fundamental frequency may be extracted from the time-domain current signal. A harmonic relationship between multiple harmonics may be determined, such as a set of ratios of the strengths of various pairs of the extracted harmonics, referred to herein as harmonic ratios. Harmonic ratios or other harmonic relationships, like the time-domain current signal, are characteristic of the analyte concentration. A harmonic ratio is a quotient of a strength of a first harmonic divided by a strength of a second harmonic. Strength may include, for example, amplitude, power, or the like. A harmonic ratio may be generated from any pair of harmonic strength values extracted from the time-domain sample data. Thus, analyte concentrations may be represented by a corresponding set of harmonic ratios. By determining the characteristic sets of harmonic ratios for particular (pre-determined) analyte concentrations, and storing those characteristic sets along with their pre-determined corresponding analyte concentrations in a database, a subsequently generated set of harmonic ratios obtained from an analyte-containing fluid having an unknown analyte concentration can then be compared to the database of harmonic ratio sets and matched to a corresponding analyte concentration value. Other harmonic relationships, in addition to or in place of harmonic ratios, may be used, as previously described.

For a fundamental frequency $f_{in}$, the harmonics are: $f_n = n \cdot f_{in}$, where n is an (integer) order of the harmonic. From the harmonic strengths, different attributes can be formed, which may be optimized to correlate to the concentration of glucose, glucose interferents and/or the sensor temperature. Example attributes may include: (1) harmonic strengths; (2) the ratio of harmonic strength to the fundamental frequency strength (e.g., to normalize out the hardware calibration of the current sensing electronics); (3) the ratio of two or more harmonic strengths, which may reduce the calibration factor in the current sensing electronics; and/or (4) any other functional relationships containing two or more harmonic strengths.

An advantage of harmonics ratios is that they yield a number of different attributes. If N is the maximum number of measurable harmonics, there are $N(N-1)/2$ different attributes which may be included in correlation functions with glucose concentration, temperature and/or glucose interferents. For example, for N=15 harmonics, there are 105 different attributes that may be used to build a more complex function, such as an index function, from harmonics ratios alone.

More generally, harmonics and their derived attributes (e.g., amplitude, power, etc.) may be used with a wide range of machine learning algorithms, including but not limited to multivariate regression, neural networks, Newton-Raphson methods or conjugate gradient optimization for analyzing analyte concentrations or other properties.

Referring to FIG. 5, example harmonic relationship database 500 includes n sets of harmonic ratios, and each set of harmonic ratios has a link, or a pointer, to a corresponding analyte concentration. Each set of harmonic ratios is an n-tuple, and can be thought of as a vector in an analyte-concentration space. In example harmonic relationship database 500 the n vectors are each m-dimensional, with the value in each of the m dimensions set by the value of a ratio of a pair of harmonic strengths. In general, any number of harmonic ratios may be used.

The n vectors are illustrated here as first, second, third, and nth vectors, 502, 506, 510, and 514 respectively. Each vector 502, 506, 510, and 514 includes m harmonic ratios, and a link, or pointer, 503, 507, 511, and 515 respectively, to a corresponding analyte concentration value 504, 508, 512, and 516.

As an example, by determining the harmonic ratios $h_{a1b1}, h_{a2b2}, h_{a3b3} \ldots h_{ambm}$ for an analyte-containing fluid, the harmonic ratios $h_{a1b1}, h_{a2b2}, h_{a3b3} \ldots h_{ambm}$ may be compared to each harmonic ratio set in harmonic relationship database 500. If, for example, harmonic ratios $h_{a1b1}, h_{a2b2}, h_{a3b3} \ldots h_{ambm}$ match harmonic ratios $h_{a1b1}-1, h_{a2b2}-1, h_{a3b3}-1 \ldots h_{ambm}-1$ for the analyte-containing sample, one may determine that the sample has an analyte concentration value of Conc.-1. Similarly, if harmonic ratios $h_{a1b1}, h_{a2b2}, h_{a3b3} \ldots h_{ambm}$ match harmonic ratios $h_{a1b1}-2, h_{a2b2}-2, h_{a3b3}-2 \ldots h_{ambm}-2$ for the analyte-containing sample, the sample has an analyte concentration value of Conc.-2, and the like. The number m of harmonic ratios per vector n may be any suitable value (e.g., 2, 3, 4, 5, 10, 15, etc., up to the size of the complete set of harmonic ratios). Any number of vectors n may be used.

In some embodiments, harmonic ratios and/or other harmonic relationships may be correlated with glucose concentrations using numerical fits such as multivariate polynomials, multi-dimensional interpolation, such as using cubic splines, between experimentally measured datasets, or the like.

FIGS. 6A-D illustrate semi-log plots of a ratio of the strength of various harmonics of a fundamental frequency of a periodic voltage signal applied to a glucose-containing fluid at three different concentrations in accordance with an example embodiment of the disclosure. Referring to FIGS. 6A, 6B, 6C, and 6D, various illustrative harmonic ratio curves are shown, respectively, for the ratio of the strength of a second harmonic to a strength of a third harmonic $h_{23}$, the ratio of the strength of the third harmonic to a strength of a fifth harmonic $h_{35}$, the ratio of the strength of a fourth harmonic to the strength of the fifth harmonic $h_{45}$, and the ratio of the strength of the second harmonic to the strength of the fourth harmonic $h_{24}$ for different glucose concentrations in a sample (e.g., 50, 100 and 300 milligrams per deciliter (mg/dl)). The strengths for the harmonics are determined by extracting the harmonics from the digitized time-domain current measurement signal (e.g., from third circuit 108 in FIG. 1A, 1B or 1C, or from sampling circuit 214 in FIG. 2 or 3), and identifying the strength (e.g., amplitude, power, etc.) of these spectral components of the digitized time-domain current measurement signals. For example, a Fourier transform, a Discrete Fourier Transform, a Fast Fourier Transform, a Goertzel Transform, etc., may be used to extract spectral components. FIGS. 6A-D indicate that for any particular glucose concentration, there is a unique set of harmonic ratio values. Thus, a given set of harmonic ratio values maps to a unique corresponding glucose concentration.

Figure 7A:
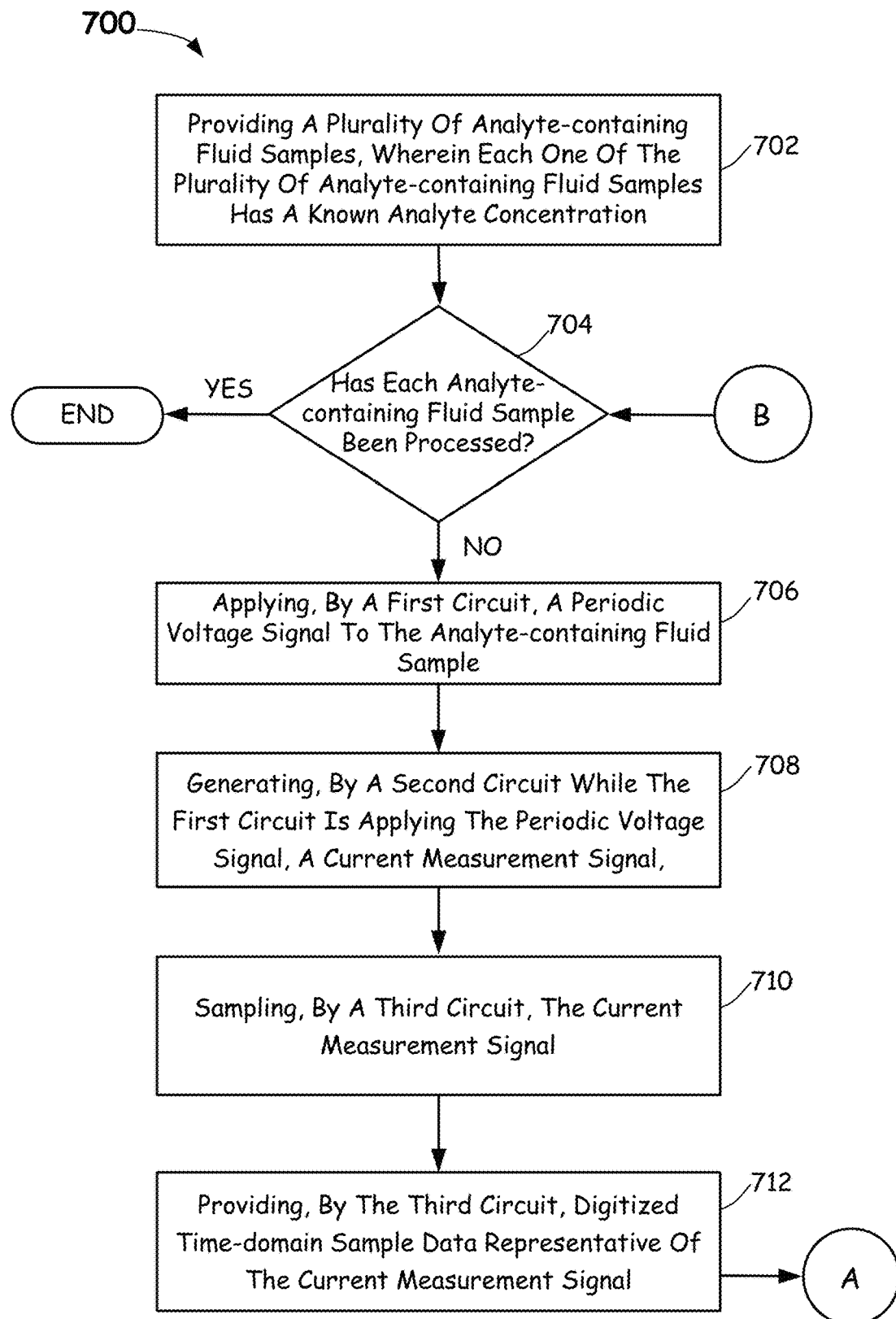
FIGS. 7A-7B illustrate a flow diagram of a method of generating a harmonic relationship database for a continuous analyte monitoring system in accordance with an example embodiment of the disclosure.
Figure 7B:
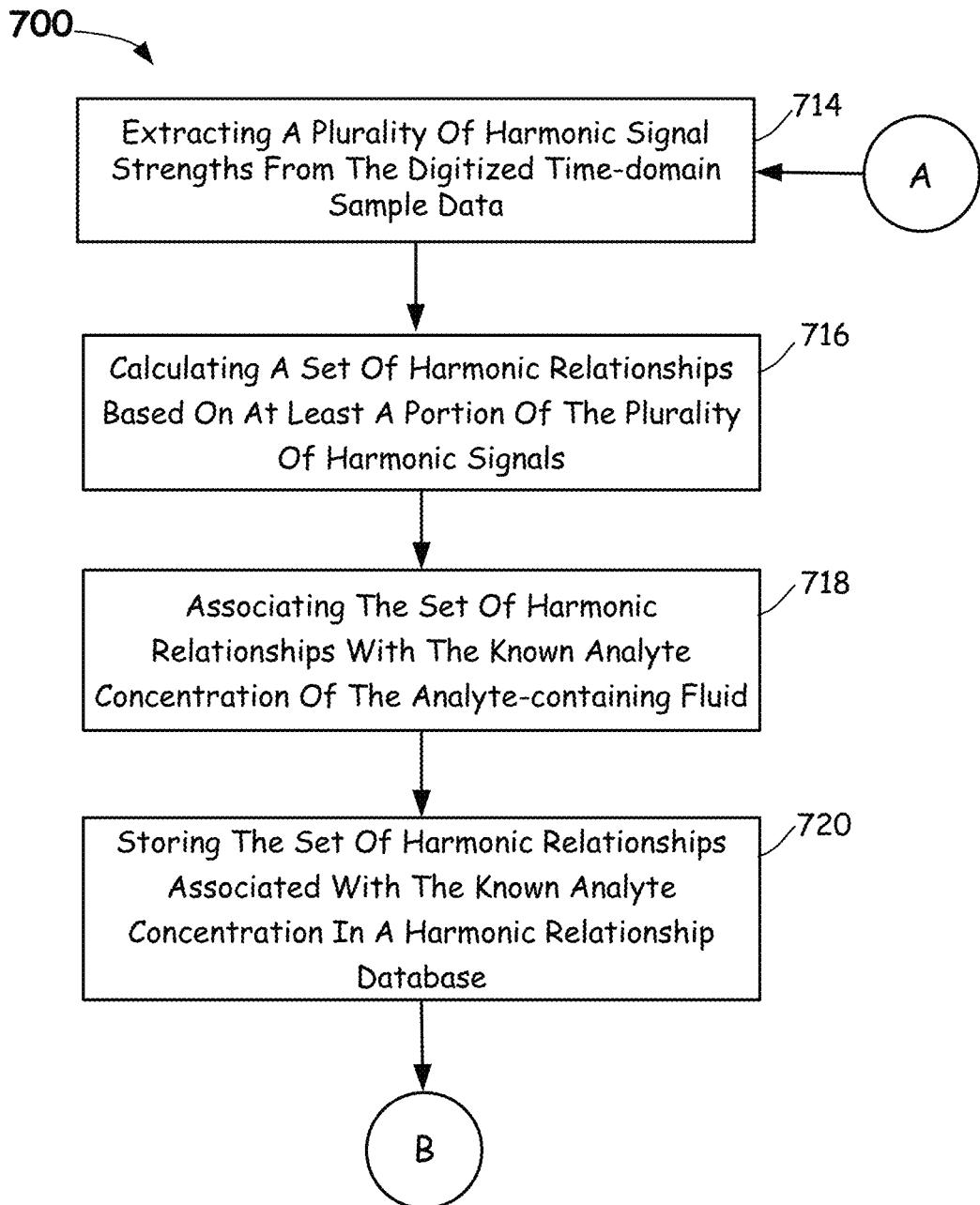

FIGS. 7A-7B illustrate a flow diagram of a method 700 of generating a harmonic relationship database for a continuous analyte monitoring system in accordance with an example embodiment of the disclosure. For example, harmonic ratios and/or other harmonic relationships may be employed. Referring first to FIG. 7A, example method 700 provides a method of producing a set of predetermined harmonic relationship information that is correlated to corresponding values of an analyte concentration in an analyte-containing fluid. In this way a harmonic relationship database may be produced that may be used, for example, in CGM products in accordance with the present disclosure to determine glucose levels in human interstitial fluids. Method 700 may include providing 702 a plurality of analyte-containing fluid samples, wherein each one of the plurality of analyte-containing fluid samples has a known analyte concentration. To produce a harmonic relationship database for glucose-containing fluids, the fluid samples contain known concentrations of glucose. In alternative embodiments, a harmonic relationship database for a different analyte may be produced by using fluid samples containing known concentrations of that analyte. Because method 700 may be used to produce a set of harmonic relationship information for each of the plurality of analyte-containing fluid samples, a decision operation 704 is performed to determine whether all of the analyte-containing fluid samples have been processed. If all the fluid samples have been processed, then method 700 ends. On the other hand, if there are more fluid samples to process, then method 700 further includes, for each one of the remaining plurality of analyte-containing fluid samples, applying 706, by a first circuit such as first circuit 102 of FIG. 1A, 1B or 1C or signal generator 206 of FIG. 2 or 3, a periodic excitation (e.g., voltage) signal (having a fundamental frequency) to the analyte-containing fluid sample. Method 700 also includes generating 708, by a second circuit while the first circuit is applying the periodic voltage signal, a current measurement signal, where the current measurement signal has a magnitude indicative of a current produced by an oxidation-reduction reaction in the analyte-containing fluid sample while the first circuit is applying the periodic voltage signal, the magnitude of the current measurement signal being dependent, at least in part, on the analyte concentration in the analyte-containing fluid sample. The second circuit may be, for example, second circuit 106 of FIG. 1A, 1B or 1C or current measuring circuit 212 of FIG. 2 or 3. Method 700 further includes sampling 710 the current measurement signal, by a third circuit, and providing 712 by the third circuit, digitized time-domain sample data representative of the current measurement signal. The third circuit may be, for example, third circuit 108 of FIG. 1A, 1B or 1C or sampling circuit 214 of FIG. 2 or 3.

The current measurement signal is a complex time-varying signal that may be represented by the summation of a series of signals each having its own frequency, amplitude, and phase characteristics, e.g., using Fourier transforms from the time-domain to the frequency-domain. The spectral content of a complex time-varying signal can be extracted, for example, by transforming a time-domain signal to a frequency-domain signal, and identifying the frequencies of the spectral peaks. Any suitable transform may be used such as a Fourier transform, a Discrete Fourier Transform, a Fast Fourier Transform, a Goertzel Transform, etc. Harmonic signals are signals having a frequency that is an integer multiple of a fundamental frequency, which in this example is the frequency of the periodic voltage signal applied to the analyte-containing fluid samples.

Referring to FIG. 7B, once the digitized time-domain sample data is available, method 700 continues by extracting 714, a plurality of harmonic signal strengths from the digitized time-domain sample data, and calculating 716 a set of harmonic relationships, such as harmonic ratios, based on at least a portion of the plurality of harmonic signals.

Each extracted harmonic signal component has a value representative of the strength, e.g., amplitude, power, etc., of its corresponding harmonic frequency. In accordance some embodiments of method 700, the harmonic relationship determined may be a harmonic ratio that is the quotient of the strengths of at least two harmonic signals (e.g., the ratio of the strengths of at least two harmonic signals). By way of example, and not limitation, a harmonic ratio may be the ratio of the strength of the third harmonic of the fundamental frequency and the fifth harmonic of the fundamental frequency. As stated, other functional relationships between harmonic signals and/or harmonic signal strengths may be used in addition to or in place of harmonic ratios. In various embodiments in accordance with the present disclosure, a plurality of harmonic relationships, such as ratios of the strengths of a plurality of harmonics, may be used to identify concentrations of at least one analyte in an analyte-containing fluid.

In some embodiments, processors and/or microcontrollers 110, 120, 222, 230 and/or 308 of FIGS. 1A-3 may perform and/or otherwise assist in harmonic extraction and/or harmonic relationship calculations, using, for example, one or more time-domain to frequency-domain transforms (e.g., forming digitized frequency-domain data). Method 700 continues by associating 718 the set of harmonic relationships with the known analyte concentration of the analyte-containing fluid, and storing 720 the set of harmonic relationships associated with the known analyte concentration in a harmonic relationship database. For example, a harmonic relationship database similar to harmonic relationship database 500 of FIG. 5 may be developed.

Figure 8:
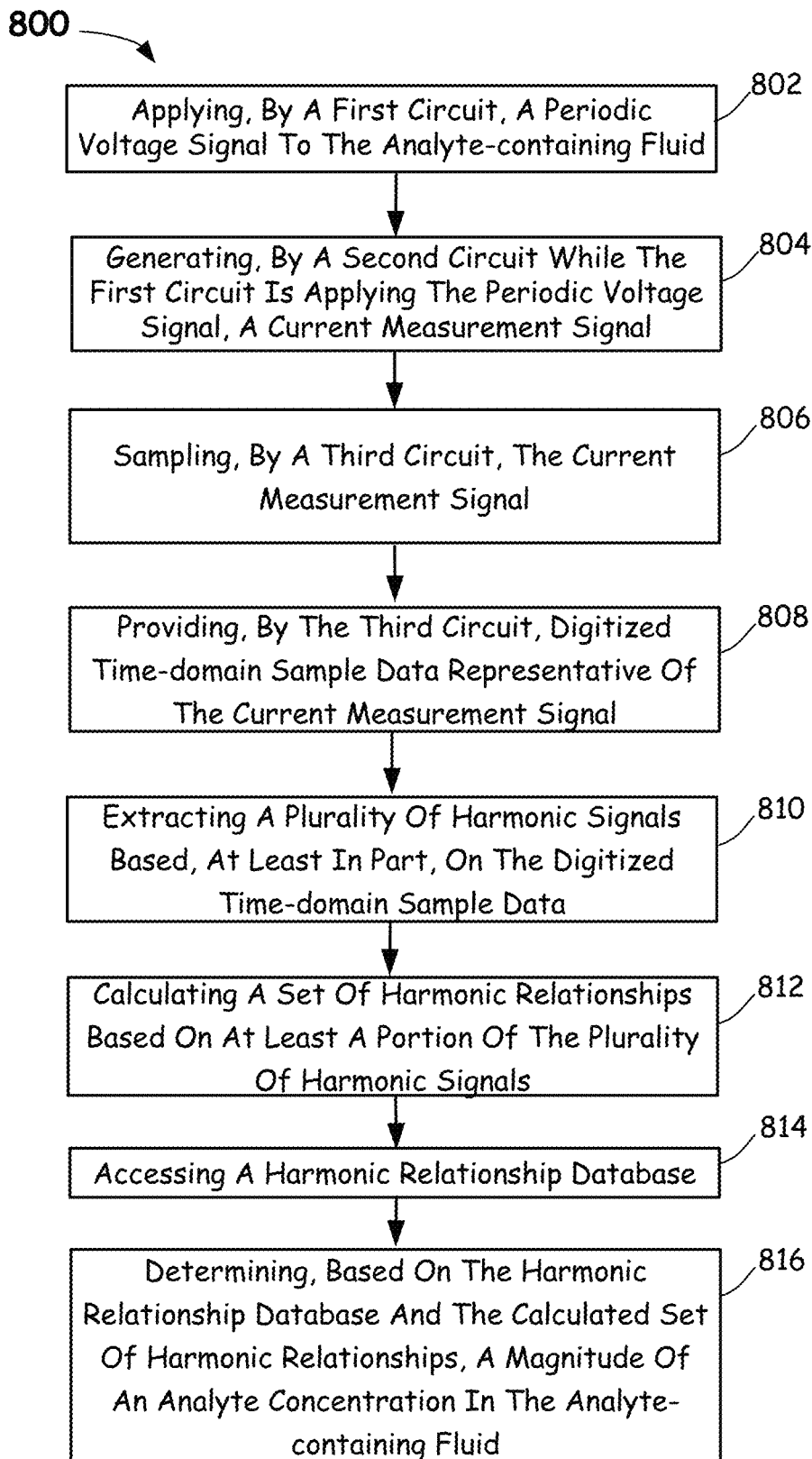
FIG. 8 illustrates a flow diagram of a method of determining an analyte concentration in accordance with an example embodiment of the disclosure.

FIG. 8 illustrates a flow diagram of a method 800 of determining an analyte concentration in accordance with an example embodiment of the disclosure. Referring to FIG. 8, example method 800 provides for electronically probing an oxidation-reduction reaction in an analyte-containing fluid to determine a concentration of at least one analyte in the fluid. Method 800 includes applying 802, by a first circuit such as first circuit 102 of FIG. 1A, 1B or 1C or signal generator 206 of FIG. 2 or 3, a periodic excitation (e.g., voltage) signal (having a fundamental frequency) to the analyte-containing fluid, and generating 804, by a second circuit while the first circuit is applying the periodic voltage signal, a current measurement signal, having a magnitude indicative of a current produced by an oxidation-reduction reaction in the analyte-containing fluid, the magnitude dependent, at least in part, on an analyte concentration in the analyte-containing fluid. The second circuit may be, for example, second circuit 106 of FIG. 1A, 1B or 1C or current measuring circuit 212 of FIG. 2 or 3. In one embodiment the analyte may be glucose, and in alternative embodiments, one or more other analytes may be in the analyte-containing fluid. Method 800 further includes sampling 806 the current measurement signal, by a third circuit, and providing 808, by the third circuit, digitized time-domain sample data representative of the current measurement signal. In some embodiments, the sampling circuit may be an A/D converter having a suitable bit resolution. The third circuit may be, for example, third circuit 108 of FIG. 1A, 1B or 1C or sampling circuit 214 of FIG. 2 or 3.

Once the digitized time-domain sample data representative of the current measurement signal is available, method 800 continues by extracting 810 a plurality of harmonic signals based, at least in part, on the digitized time-domain sample data, wherein the harmonic signals are harmonics of the fundamental frequency, and each harmonic signal has a corresponding strength. Method 800 continues by calculating 812 a set of harmonic relationships of at least two harmonic strengths, such as harmonic ratios, based on at least a portion of the plurality of harmonic signals that have been extracted, and accessing 814 a harmonic relationship database, wherein the harmonic relationship database includes a plurality of sets of harmonic relationships (see, for example, FIG. 5), each set of harmonic relationships associated with a corresponding analyte concentration. Method 800 further includes determining 816, based on the harmonic relationship database and the calculated set of harmonic relationships, an analyte concentration in the analyte-containing fluid. In some embodiments, determining the analyte concentration includes comparing the calculated set of harmonic relationships to one or more vectors in the harmonic relationship database (e.g., harmonic relationship database 500 of FIG. 5), and when a match is found between the calculated set of harmonic relationships and a vector in the harmonic relationship database, following the link, or pointer, associated with the matching vector to an associated analyte concentration value. In some embodiments, processors and/or microcontrollers 110, 120, 222, 230 and/or 308 of FIGS. 1A-3 may perform and/or otherwise assist in harmonic extraction, harmonic relationship calculations, and/or determining the analyte concentration by comparing the calculated set of harmonic relationships to one or more vectors in a harmonic relationship database.

In some embodiments, harmonic ratios and/or other harmonic relationships may be correlated with analyte concentrations using numerical fits such as multivariate polynomials, multi-dimensional interpolation, such as using cubic splines, between experimentally measured datasets, or the like. Further, in some embodiments, harmonics and their derived attributes (e.g., amplitude, power, etc.) may be used with a wide range of machine learning algorithms, including but not limited to multivariate regression, neural networks, Newton-Raphson methods or conjugate gradient optimization for analyzing analyte concentrations or other properties.

Figure 9:
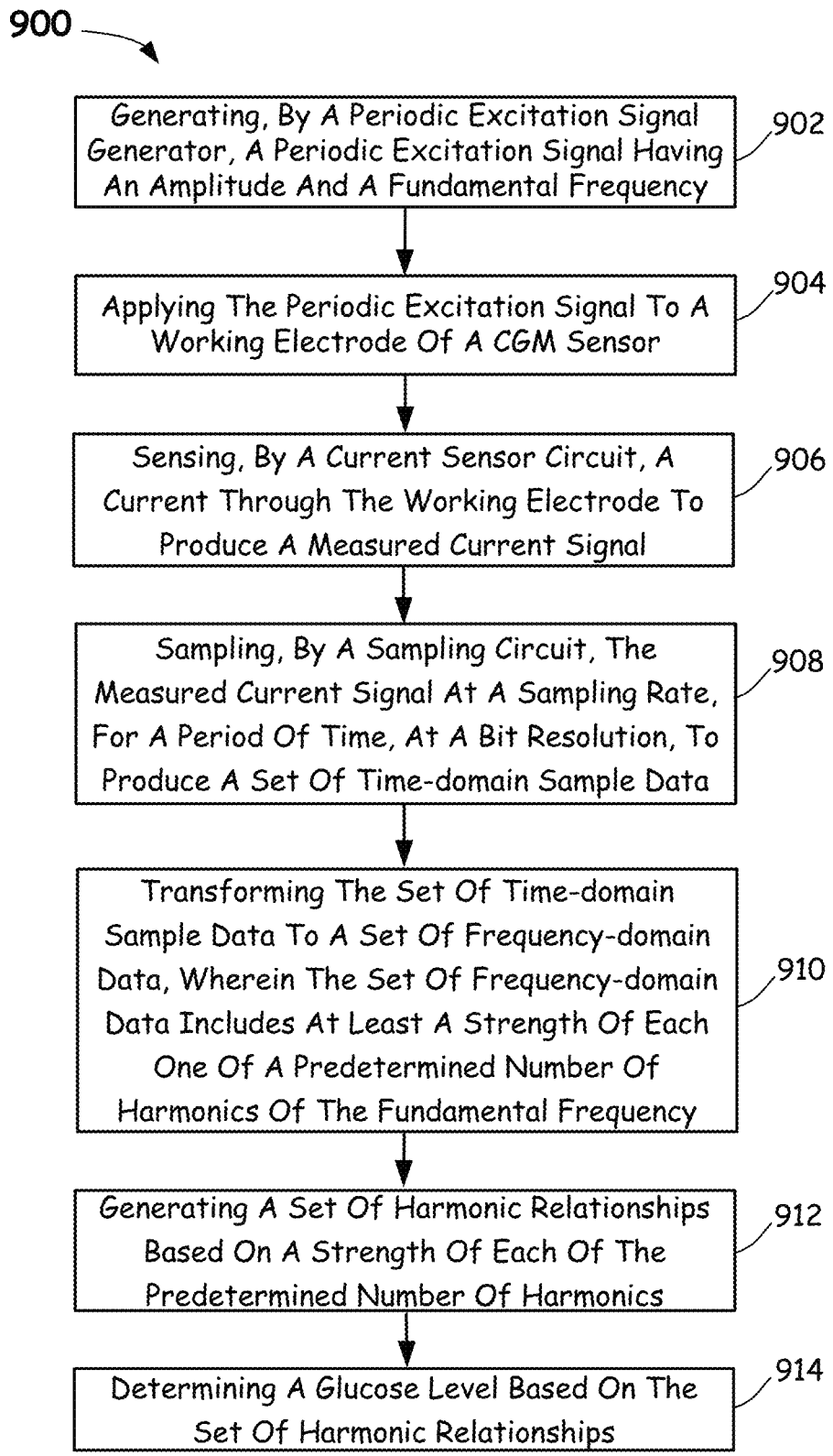
FIG. 9 illustrates a flow diagram of a method of continuous glucose monitoring in accordance with an example embodiment of the disclosure.

FIG. 9 illustrates a flow diagram of a method 900 of continuous glucose monitoring in accordance with an example embodiment of the disclosure. Referring to FIG. 9, after a CGM sensor is inserted under a person's skin, and a wearable portion of a CGM system is adhered to the person's skin, method 900 provides generating 902, by a periodic excitation signal (e.g., an AC excitation signal, a periodic voltage signal, etc.) generator, a periodic signal having an amplitude and a fundamental frequency, and applying 904 the excitation signal to an electrode of the CGM sensor. Method 900 continues by sensing 906, with a current sensor circuit, a current through the CGM sensor to produce a measured current signal. The measured current signal is dependent, at least in part, on the excitation signal, and at least in part on the glucose concentration in the person's interstitial fluid. Method 900 continues by sampling 908, with a sampling circuit, the measured current signal at a sampling rate, for a period of time, and at a bit resolution, to produce a set of time-domain sample data. In various embodiments, the sampling rate is greater than the fundamental frequency of the excitation signal, for example, but not limited to, fifty times greater, one hundred times greater, or even two hundred times greater, or even four hundred times greater. Method 900 continues by transforming 910 the set of time-domain sample data to a set of frequency-domain data, wherein the set of frequency-domain data includes a strength of each one of a predetermined number of harmonics of the fundamental frequency. Method 900 further includes generating 912 a set of harmonic relationships based on a strength of each of the predetermined number of harmonics. Method 900 further includes determining 914 a glucose level (e.g., concentration) based on the set of harmonic relationships. As noted above, in some embodiments, the set of harmonic relationships may map to a concentration of glucose within a harmonic relationship database. Method 900 may be performed, for example, by one or more of CGM systems 100, 150, 170, 200 or 300.

In some embodiments, the frequency of the periodic excitation signal applied to an analyte-containing fluid may be selected based, at least in part, on an approximate concentration of analyte in the analyte-containing fluid. For example, an approximate analyte concentration may be an expected analyte concentration (e.g., based on typical observed analyte concentrations for a patient, previous concentrations levels measured for the patient, time of day, when and/or what a patient last ate, etc.). In some embodiments, a simple DC or other analyte concentration measurement may be performed to determine an approximate analyte concentration.

Based on approximate concentration of analyte in the analyte-containing fluid, the fundamental frequency of the periodic excitation signal may be determined. For example, for glucose, if the approximate analyte (e.g., glucose) concentration indicates an intermediate glucose concentration is present in a fluid to be analyzed, a frequency of about 0.5 to 1.5 Hz may be used for the periodic excitation signal. As another example, if the approximate analyte (e.g., glucose) concentration indicates a low glucose concentration is present in a fluid to be analyzed, a frequency of about 4.5 to 5.5 Hz may be used for the periodic excitation signal. Other frequencies may be used for these and/or other analyte concentrations. In some embodiments, basing selection of the frequency of the periodic excitation signal at least in part on an approximate analyte concentration may provide a more-accurate frequency domain based determination of analyte concentration.

Figure 10:
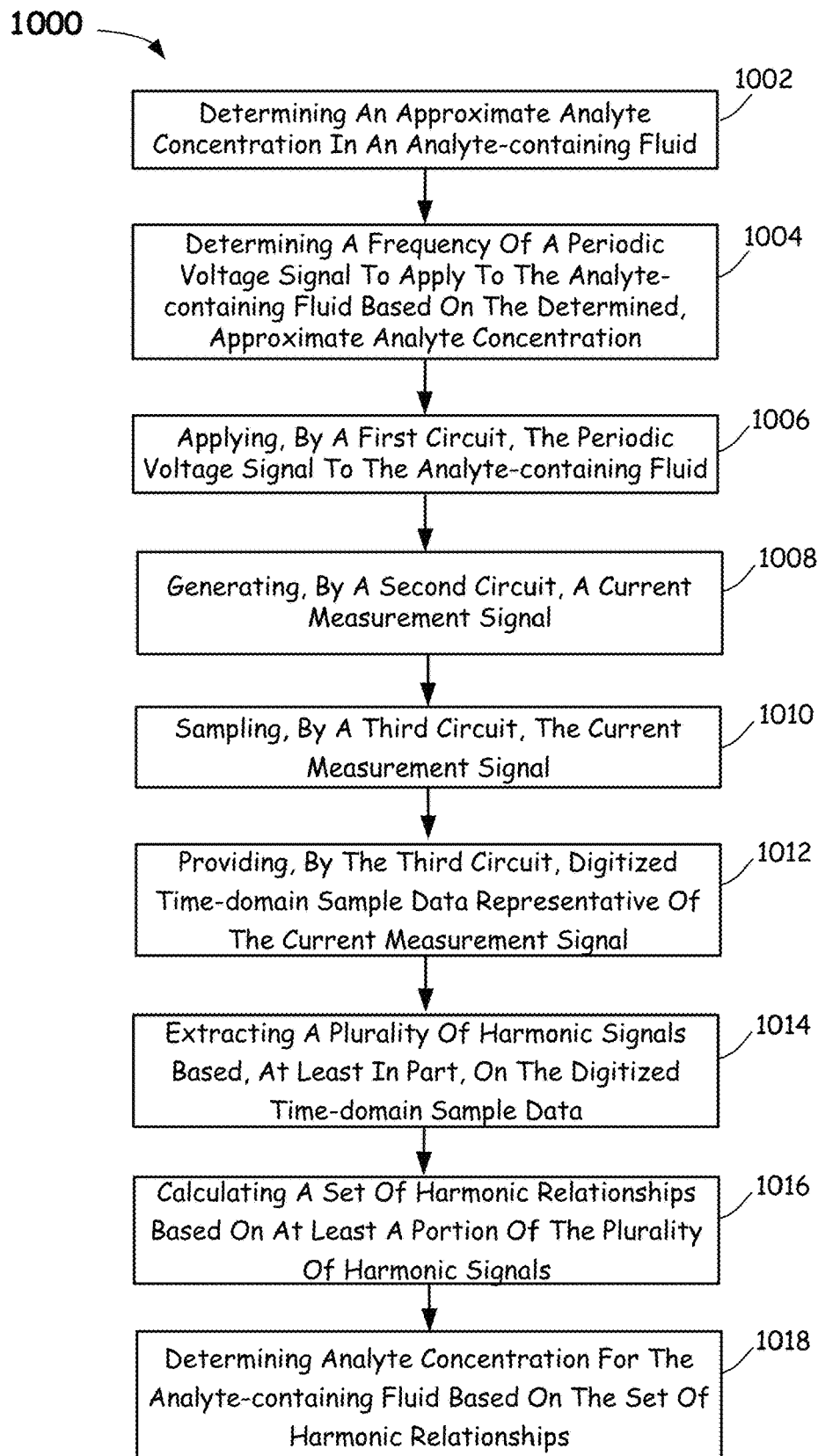
FIG. 10 illustrates a flow diagram of another example method of analyte-concentration monitoring in accordance with embodiments of the disclosure.

FIG. 10 illustrates a flow diagram of a method 1000 of analyte-concentration monitoring in accordance with an example embodiment of the disclosure. Referring to FIG. 10, to determine an analyte concentration in an analyte-containing fluid, method 1000 provides determining 1002 an approximate analyte concentration for the analyte-containing fluid. As described above, this may include employing an expected analyte concentration, employing a simple DC analyte concentration measurement, or the like, to obtain an estimated or approximate analyte concentration level. Method 1000 then includes determining 1004 a frequency of a periodic excitation (e.g., voltage) signal to apply to the analyte-containing fluid based on the approximate analyte concentration. For example, in some embodiments, a higher frequency may be used for low analyte concentrations than for medium or high analyte concentrations. Method 1000 then includes applying 1006 the periodic signal to the analyte-containing fluid and generating 1008 a current measurement signal. The measured current signal is dependent, at least in part on the excitation signal, and at least in part on the analyte concentration in the analyte-containing fluid. Method 1000 continues by sampling 1010 the measured current signal to produce 1012 a set of time-domain sample data. In various embodiments, the sampling rate is greater than the fundamental frequency of the excitation signal, for example, but not limited to, fifty times greater, one hundred times greater, or even two hundred times greater, or even four hundred times greater. Method 1000 continues by extracting 1014 a plurality of harmonic signals based, at least in part, on the digitized time-domain sample data and calculating 1016 a set of harmonic relationships based on at least a portion of the plurality of harmonic signals. For example, harmonic ratios and/or other combinations of two or more harmonic strengths may be employed to form a set of harmonic relationships. Method 1000 then includes determining 1018 analyte concentration for the analyte-containing fluid based on the set of harmonic relationships. In some embodiments, a harmonic relationship database, multivariate polynomials, multi-dimensional interpolation, such as using cubic splines, or the like may be used to determine analyte concentration. Method 1000 may be performed, for example, by one or more of the monitoring systems 100, 150, 170, 200 or 300, for example.

As described, the methods and systems described herein may be employed to determine concentration of analytes other than glucose, such as maltose, galactose, hematocrit, etc., interferents of such analytes, concentration of medications such as acetaminophen, or the like.

One of the main challenges in continuous glucose monitoring is the calibration of the sensors in the interstitial fluid.

Ratios or other relationships of at least two harmonic strengths as algorithm attributes may have less dependence on calibration compared to utilizing absolute current measurements. Compared to DC measurements, which yield one data point for one measurement, the advantage of an algorithm with a basis function set built upon the relationships of harmonics is that many harmonics (typically in the range of 10-20, or more) can be extracted, and the ratios or other functional relations among all these harmonics may represent hundreds of independent concurrent measurements. The harmonics may be extracted from any time range which is an integer multiple of the fundamental period of the excitation pulse. Because the use of relationships of harmonics is primarily calibration independent, the bit resolution of the A/D converter stage may be relaxed, reducing component cost and possibly complexity of the analog front end. The harmonics-based algorithm is scalable, allowing optimized deployment on different CPU platforms, ranging from efficient Goertzel transforms on small microcontrollers to full-scale, real-time Fourier analysis for higher-performance processors.

As described herein, the non-linear components in the current response are dependent on the glucose concentration in a repeatable manner. One way to quantify the non-linear contribution is through the extraction of higher harmonics of the fundamental frequency:

$$f_n = n * f_{in}, \quad [1]$$

where n is the order of the integer harmonic;

Embodiments described herein may include extracting the amplitude or power component of a number of harmonic orders in the spectrum of the current through a working electrode (e.g., including harmonics from n=2 to beyond the order of n=10). Any suitable numerical method to extract the entire spectrum, or only the contribution of specific frequencies, may be used, including but not limited to discrete Fourier transform, fast Fourier transform or Goertzel transform. For example, the discrete Fourier transform based on equation [1] yields:

$$S_k = \Sigma_{tbins=0}^{timebins} V_{meas,k}(tbin) * \exp(-2\pi i * tbin^k / timebins) \quad [2],$$

where timebins is the sampling interval, and $$k/timebins = nf_{in}t \quad [3]$$

The Fourier transform $S_k$ from equation [2], extracted at the harmonic frequencies $f_n$ from equation [3] may be referred to as harmonic strength $h_n$. From the harmonic strengths, different attributes may be formed, which are optimized to be correlated to the concentration of glucose, glucose interferents and/or the sensor temperature, where the correlation may be described through the most straightforward functional relationship. The attributes may include, for example, the harmonic strengths $h_n$ proper, the ratio of the harmonic strength to the fundamental: $h_{n1} = h_n/h_1$, the ratio of two harmonic strengths: $h_{nm} = h_n/h_m$, and/or any other functional relationship containing two or more harmonic strengths. Regarding the ratio of the harmonic strength to the fundamental, $h_{n1} = h_n/h_1$, the advantage of this approach is to substantially normalize out the hardware calibration of the current sensing electronics. For example, if any DC offset is removed (e.g., if the extraction of the harmonics is set up as a well-conditioned digital filter), no absolute calibration of the current sensing electronics may e necessary. Regarding the ratio of two harmonic strengths: $h_{nm} = h_n/h_m$, this may yield similar advantages, such as the elimination of the calibration factor in the current sensing electronics. Furthermore, the harmonics ratios yield a number of N(N−1)/2 different attributes, which may be included in correlation functions with the glucose, temperature or glucose interferents, where N is the maximum number of measureable harmonics. For N=15, 105 different attributes may be used to build more complex functions, such as index functions, from the simple harmonics ratios alone.

Embodiments disclosed herein may provide continuous measurements of the concentration of reagents in aqueous solutions by monitoring the ratios of harmonics in the current through the working electrode of a sensor. Continuous monitoring of numerous current harmonics permits self-calibration of signals in a CGM (e.g., without the need for DC current measurements and frequent calibrations). The attributes extracted using harmonics may eliminate the absolute current scale, decreasing the demands on (and cost of) sensor electronics and calibration. Attributes are independent of acquisition and can be readily analysed with any suitable algorithm.

The above described embodiments may be implemented as a continuous algorithm, such as, for example, through a digital filter. Any operation on a continuous data stream can be described as a filter, such as a finite impulse response (FIR) filter, an infinite impulse response (IIR) filter or a recursive response (RR) filter. The exact implementation may depend on the processing environment the algorithm will be deployed on, as well as the number of harmonics to be extracted. Combining the generic definition of an FIR filter with the Fourier transform in equation [2] above, yields:

$$Y_k = \Sigma_{timebin=0}^{timebins} b_{timebin,k} I_{meas}(-timebin) \quad [4]; \text{ and}$$

$$b_{timebin,k} = \exp(-2\pi i * tbin^k / timebins) \quad [5]$$

where there is a set of FIR coefficients $b_{timebin,k}$ for each frequency mode k, which are integrated "looking back" in time. For a moderate number of frequencies extracted, the Fourier transform in equation [4] may be updated by adding the "newest" term $b_{timebin,k} I_{meas}$ (−timebin) for timebin=0, and subtracting the "oldest", for timebin=timebins. This will yield the fastest reaction time to changes in the measured current, but may not be the most optimal approach if the extraction of a large number of frequencies is desired. In the latter case, a batch algorithm such as the Fast Fourier Transform (FFT) may be used, which may be applied on a window ("timebins" in equations [4] and [5]), but with the periodicity of application far longer than the sampling time (e.g., determined by the expected rate of change of, in this case, the underlying chemistry). For example, in a CGM scenario, an FFT may be applied every 1-5 minutes, on data windows covering less (possibly much less, such as a few seconds for severe CPU constraints) than 1-5 minutes. In yet other cases, in which only a few harmonics are extracted, the Goertzel transform may be employed.

Embodiments described herein may provide a more efficient method to perform measurements of glucose and possibly other analyte concentrations in a continuous acquisition and signal processing mode, yielding time-domain measurements which are delayed from ground truth in the interstitial fluid by a time interval which is small compared to the delay between arterial blood and interstitial fluid. The algorithm is compatible with any implementation of predictive modeling of hypo/hyperglycemic events (e.g., linear regression, auto-regressive predictive modeling, Kalman filtering or artificial neural networks). In some embodiments, predictive modeling may be employed to generate one or more prediction equations that employ one or more sets of harmonic relationships, such as harmonic ratios, to determine analyte concentration during continuous analyte sensing (e.g., in place of or in addition to the use of a harmonic relationship database). For example, in some embodiments, multivariate regression may be employed with known analyte concentration as the regression target and a large number of harmonic relationships, such as harmonic ratios and/or other terms and/or cross terms, as the input parameters providing information gathered from the non-linear current response to a periodic excitation signal. In some embodiments, one or more of such prediction equations may be stored in a memory of a continuous analyte sensing device and used to compute analyte values through use of harmonic relationships during continuous analyte sensing. For example, one or more prediction equations may be stored in memory 112, 228 and/or 302 of CGM systems 100, 150, 170, 200 or 300.

One of the main challenges in continuous glucose monitoring is the calibration of the sensors in the interstitial fluid. Ratios or other relationships of harmonics as algorithm attributes may result in a much lowered dependence of the algorithm on the calibration compared to utilizing absolute current measurements. Compared to DC measurements, which yields one data point for one measurement, the advantage of the embodiments described herein, is that many harmonics (typically in the range of 10-20) may be extracted, and the ratios or other functional relations among all these harmonics may comprise on the order of hundreds of truly independent concurrent measurements. As opposed to many existing algorithms derived from BGM measurements, embodiments described herein demonstrate algorithms which may be time-invariant (e.g., a glucose value may be extracted from any time range which is an integer multiple of the period of the excitation pulse). The use of ratios of harmonics may eliminate the need for an "absolute" sensor calibration, relaxing the bit resolution of the analog-to-digital converter stage and reducing component cost and possibly complexity of the analog front end. The algorithm is very scalable, allowing optimized deployment on different CPU platforms, ranging from efficient Goertzel transforms on small microcontrollers to full-scale, real-time Fourier analysis for higher-performance processors.

In some embodiments, phase angle and/or power spectral density data may be generated from the digitized frequency-domain data and used for harmonic strength information.

In some embodiments, the non-wearable portion of an analyte monitoring system may include a mobile telephone, such as a smartphone, a smartwatch, or the like.

As described above in connection with FIG. 1A, various electronic components and circuits are configured to couple to a power supply, such as but not limited to, a battery. In some embodiments, an alternative to a battery may include a supercapacitor. In some embodiments, one or more energy harvesting circuits, such as the class of ubiquitous energy harvesting circuits well known for their use in RFID tags, may be used to charge a capacitor or a supercapacitor, which in turn acts as battery. The well-known class of energy harvesting circuits are configured to convert energy from an RF energization field into a regulated DC voltage. In some alternative embodiments a charging current for a capacitor or supercapacitor may be supplied by a thermoelectric generator. The temperature gradient required to produce a voltage by the thermoelectric generator may be obtained from the difference between the skin of the user at that point of CGM attachment, and a distal end of the CGM disposed away from the point of attachment, for example.

The term "amperometry," as used herein, refers to the detection of ions in a solution, where that detection is based, at least in part, on sensing an electric current, or sensing changes in the electric current.

A "processor" means any one or more microprocessors, one or more Central Processing Units (CPUs), one or more Graphics Processing Units (GPUs), one or more computing devices, one or more microcontrollers, one or more digital signal processors (DSPs), one or more embedded processors such as an embedded processor in a System on Chip (SoC), one or more field programmable gate arrays (FPGAs), like devices, or various combinations of the foregoing.

While it is contemplated that an appropriately programmed general purpose computer or computing device may be used, it is also contemplated that hard-wired circuitry or custom hardware (e.g., an application specific integrated circuit (ASIC)) may be used in place of, or in combination with, software instructions for implementation of the processes of various embodiments. Thus, embodiments are not limited to any specific combination of hardware and software.

The term "computer-readable medium" refers to any statutory medium that participates in providing data (e.g., instructions) that may be read by a computer, a processor or a like device. Such a medium may take many forms, including but not limited to non-volatile media, volatile media, and specific types of transmission media. Non-volatile media may include, for example, optical disks, magnetic disks, and other persistent memory. Volatile media may include, but are not limited to, static random access memory (SRAM), and dynamic random access memory (DRAM). Types of transmission media may include, for example, coaxial cables, electrically conductive wires, traces, or lines, including the wires, traces, or lines, that comprise a system bus coupled to the processor, and optical fibers. Common forms of computer-readable media may include, for example, a floppy disk, a flexible disk, a hard disk, a magnetic tape, any other magnetic medium, a CD-ROM, a Digital Video Disc (DVD), any other optical medium, punch cards, paper tape, any other physical medium with patterns of holes, a read-only memory (ROM), a random access memory (RAM), a programmable read-only memory (PROM), an electrically programmable read-only memory (EPROM), an electrically erasable programmable read-only memory (EEPROM), a flash memory (a type of EEPROM), a resistive memory, a filamentary memory, a metal oxide memory, a phase change memory, a spin transfer memory, a USB memory stick, any other memory chip or cartridge, or any other medium from which a computer, or processor, can access the data or instructions stored therein. As used herein, the terms "computer-readable memory" and/or "tangible media" specifically exclude signals, waves, and wave forms or other intangible or transitory media that may nevertheless be readable by a computer.

The term "nominal" as used herein refers to a desired, or target, value of a characteristic, measurement, or other parameter for a component, product, signal, or process, together with a range of values above or below the desired value. The range of values is typically due to slight variations in manufacturing processes, or tolerances.

As used herein, "or" is meant as an inclusive or, and not as an exclusive or. That is, as used herein, A or B, is meant to include A alone, B alone, and A and B together. In the case where A alone, B alone, and not A and B together, is meant to be expressed, this will be explicitly stated. At least one of A and B is meant to include A alone, B alone and A and B.

An enumerated list of items (which may or may not be numbered) does not imply that any or all of the items are mutually exclusive, unless expressly specified otherwise. Likewise, an enumerated list of items (which may or may not be numbered) does not imply that any or all of the items are comprehensive of any category, unless expressly specified otherwise. For example, the enumerated list "a computer, a laptop, a smartphone," does not imply that any or all of the three items of that list are mutually exclusive and does not imply that any or all of the three items of that list are comprehensive of any category.

Although the terms first, second, etc., may be used herein to describe various elements, components, regions, parts or sections, these elements, components, regions, parts or sections, should not be limited by these terms. The terms may be used to distinguish one element, component, region, part or section, from another element, component, region, part or section. For example, a first element, component, region, part or section discussed above could be termed a second element, component, region, part or section without departing from the teachings of the present disclosure. First, second or third circuits may be subcomponents of one or more other circuits.

The foregoing description discloses only example embodiments. Modifications of the above-disclosed apparatus and methods which fall within the scope of this disclosure will be readily apparent to those of ordinary skill in the art.

What is claimed is:

1. A method of electronically probing an oxidation-reduction reaction in an analyte-containing fluid, comprising:
    applying, by a first circuit, a periodic excitation signal to the analyte-containing fluid, wherein the periodic excitation signal has a fundamental frequency;
    generating, by a second circuit while the first circuit is applying the periodic excitation signal, a current measurement signal, wherein the current measurement signal has a magnitude indicative of a current produced by an oxidation-reduction reaction in the analyte-containing fluid, the magnitude dependent, at least in part, on an analyte concentration in the analyte-containing fluid;
    sampling, by a third circuit, the current measurement signal;
    providing, by the third circuit, digitized time-domain sample data representative of the current measurement signal;
    extracting a plurality of harmonic signals based, at least in part, on the digitized time-domain sample data, wherein the harmonic signals are harmonics of the fundamental frequency, and each harmonic signal has a corresponding strength;
    calculating a set of harmonic relationships based on at least a portion of the plurality of harmonic signals;
    accessing a harmonic relationship database, wherein the harmonic relationship database includes a plurality of sets of harmonic relationships, each set of harmonic relationships associated with a corresponding analyte concentration; and
    determining, based on the harmonic relationship database and the calculated set of harmonic relationships, a magnitude of the analyte concentration in the analyte-containing fluid.

2. The method of claim 1, wherein extracting the plurality of harmonic signals comprises:
    transforming the digitized time-domain sample data to digitized frequency-domain data.

3. The method of claim 2, further comprising:
    generating power spectral density data from the digitized frequency-domain data.

4. The method of claim 1, wherein accessing the harmonic relationship database comprises:
    accessing a lookup table.

5. The method of claim 1, further comprising:
    wirelessly transmitting the digitized time-domain sample data representative of the current measurement signal from a first apparatus to a second apparatus.

6. The method of claim 5, wherein the first apparatus is a wearable continuous glucose monitoring device, and the second apparatus is a smartphone.

7. The method of claim 1, wherein sampling the current measurement signal includes sampling at a first sampling rate for a first period of time.

8. The method of claim 7, wherein the first sampling rate is in a range of 10 samples per second to 1000 samples per second.

9. The method of claim 8, wherein the first period of time is in a range of 10 seconds to 300 seconds.

10. The method of claim 1, wherein the fundamental frequency of the periodic excitation signal is in a range of 0.1 Hz to 10 Hz.

11. The method of claim 10, wherein the periodic excitation signal has an amplitude in a range of 150 millivolts to 500 millivolts.

12. The method of claim 1, wherein the analyte-containing fluid comprises glucose.

13. The method of claim 1 wherein determining the magnitude of the analyte concentration in the analyte-containing fluid is performed by a wearable portion of an analyte monitoring system.

14. The method of claim 13 further comprising displaying the analyte concentration in the analyte-containing fluid on a display of the wearable portion.

15. The method of claim 1 further comprising increasing a number of cycles of the periodic excitation signal to improve signal-to-noise ratio.

16. The method of claim 1 further comprising employing the calculated harmonic relationships to distinguish an analyte from at least one analyte interferent.

17. The method of claim 1, further comprising:
    determining an approximate analyte concentration in the analyte-containing fluid; and
    selecting the fundamental frequency of the periodic excitation signal based at least in part on the determined approximate analyte concentration.

18. A continuous analyte monitoring (CAM) system, comprising:
    a first circuit configured to apply a periodic excitation signal to an analyte-containing fluid;
    a second circuit configured to generate a current measurement signal, the current measurement signal having a magnitude indicative of a current in the analyte-containing fluid, the magnitude dependent, at least in part, on an analyte concentration in the analyte-containing fluid;
    a third circuit configured to sample the current measurement signal, and further configured to produce digitized time-domain sample data; and
    a processor coupled to a memory, the memory having a harmonic relationship database stored therein, and further having instructions stored therein that, when executed by the processor, cause the processor to:
        extract a plurality of harmonic signals from the digitized time-domain sample data;

calculate a set of harmonic relationships based on at least a portion of the plurality of harmonic signals;

access the harmonic relationship database, wherein the harmonic relationship database includes a plurality of sets of harmonic relationships, each set of harmonic relationships associated with a corresponding analyte concentration; and determine, based on the harmonic relationship database and the calculated set of harmonic relationships, a magnitude of the analyte concentration in the analyte-containing fluid.

19. The CAM system of claim 18, wherein the first circuit, the second circuit, and the third circuit, are disposed in a wearable device.

20. The CAM system of claim 19, wherein the processor, and the memory are disposed in the wearable device.

21. The CAM system of claim 18, wherein the instructions when executed by the processor further cause the processor to transform the digitized time-domain sample data to frequency domain data.

22. The CAM system of claim 18, wherein the instructions when executed by the processor further cause the processor to direct a wireless transmitter to transmit the analyte concentration in the analyte-containing fluid.

* * * * *